(12) United States Patent
Wong et al.

(10) Patent No.: US 8,894,578 B2
(45) Date of Patent: Nov. 25, 2014

(54) IMPLANTABLE MEMS INTRAOCULAR PRESSURE SENSOR DEVICES AND METHODS FOR GLAUCOMA MONITORING

(75) Inventors: Vernon G. Wong, Menlo Park, CA (US); Douglas A. Lee, Menlo Park, CA (US)

(73) Assignee: Orthomems, Inc., Menlo Park, CA (US)

( * ) Notice: Subject to any disclaimer, the term of this patent is extended or adjusted under 35 U.S.C. 154(b) by 0 days.

(21) Appl. No.: 13/414,069

(22) Filed: Mar. 7, 2012

(65) Prior Publication Data

US 2012/0226133 A1 Sep. 6, 2012

Related U.S. Application Data

(63) Continuation of application No. PCT/US2010/049461, filed on Sep. 20, 2010.

(60) Provisional application No. 61/243,847, filed on Sep. 18, 2009, provisional application No. 61/335,562, filed on Jan. 8, 2010.

(51) Int. Cl.
*A61B 3/16* (2006.01)
*A61B 5/00* (2006.01)

(52) U.S. Cl.
CPC .............. *A61B 3/16* (2013.01); *A61B 2562/028* (2013.01); *A61B 5/6846* (2013.01)
USPC .......................................... 600/398; 600/399

(58) Field of Classification Search
CPC ....... A61B 3/16; A61B 3/165; A61F 9/00781
USPC .................................................. 600/398, 399
See application file for complete search history.

(56) References Cited

U.S. PATENT DOCUMENTS

| 4,501,274 A | 2/1985 | Skjaerpe |
| 5,005,577 A | 4/1991 | Frenkel |

(Continued)

FOREIGN PATENT DOCUMENTS

| CN | 1486158 A | 3/2004 |
| CN | 101466299 A | 6/2009 |

(Continued)

OTHER PUBLICATIONS

U.S. Appl. No. 13/232,300, filed Sep. 14, 2011, Wong et al.

(Continued)

*Primary Examiner* — Sean Dougherty
*Assistant Examiner* — Daniel Cerioni
(74) *Attorney, Agent, or Firm* — Wilson Sonsini Goodrich & Rosati

(57) ABSTRACT

An implantable device for measuring IOP comprises a distal portion, a proximal portion and a conformable elongate support extending between the distal and proximal portions. The distal portion comprises a pressure sensor, for example a capacitor, and the proximal portion comprises a coil. The conformable elongate support extends between the distal portion and the coil so as to couple the distal portion to the coil, and the conformable elongate support is sized to position the sensor in the anterior chamber when the proximal portion is positioned under a conjunctiva of the eye. Positioning of the pressure sensor in the anterior chamber has the benefit of readily accessible surgical access and a direct measurement of the IOP of the eye. The proximal portion comprising the coil can be configured to place the coil between the sclera and the conjunctiva, such that the invasiveness of the surgery can be decreased substantially.

21 Claims, 22 Drawing Sheets

(56) References Cited

U.S. PATENT DOCUMENTS

| | | | |
|---|---|---|---|
| 5,879,319 | A | 3/1999 | Pynson et al. |
| 6,213,943 | B1 | 4/2001 | Abreu |
| 6,443,893 | B1 | 9/2002 | Schnakenberg et al. |
| 6,447,449 | B1 | 9/2002 | Fleischman et al. |
| 6,579,235 | B1 | 6/2003 | Abita et al. |
| 6,682,490 | B2 | 1/2004 | Roy et al. |
| 6,706,005 | B2 | 3/2004 | Roy et al. |
| 6,796,942 | B1 | 9/2004 | Kreiner et al. |
| 6,890,300 | B2 | 5/2005 | Lloyd et al. |
| 6,939,299 | B1 | 9/2005 | Petersen et al. |
| 7,678,065 | B2 | 3/2010 | Haffner et al. |
| 8,475,374 | B2 | 7/2013 | Irazoqui et al. |
| 2002/0049374 | A1 | 4/2002 | Abreu |
| 2005/0020896 | A1 | 1/2005 | Fuller et al. |
| 2005/0049578 | A1* | 3/2005 | Tu et al. ............. 604/890.1 |
| 2006/0085013 | A1 | 4/2006 | Dusek et al. |
| 2007/0123767 | A1 | 5/2007 | Montegrande et al. |
| 2007/0197893 | A1 | 8/2007 | Nakai et al. |
| 2008/0015421 | A1 | 1/2008 | Penner |
| 2008/0103381 | A1 | 5/2008 | Kontiola |
| 2009/0076367 | A1 | 3/2009 | Sit et al. |
| 2009/0203985 | A1 | 8/2009 | Ehrecke |
| 2011/0071458 | A1* | 3/2011 | Rickard ........................ 604/9 |

FOREIGN PATENT DOCUMENTS

| | | |
|---|---|---|
| EP | 0321097 A2 | 6/1989 |
| EP | 0321097 A3 | 5/1991 |
| WO | WO 2009/081031 A2 | 7/2009 |
| WO | WO 2009/081031 A3 | 9/2009 |
| WO | WO 2011/035228 A1 | 3/2011 |
| WO | WO 2011/035262 A1 | 3/2011 |

OTHER PUBLICATIONS

U.S. Appl. No. 13/414,063, filed Mar. 7, 2012, Wong et al.
International search report and written opinion dated Jan. 31, 2011 for PCT/US2010/049527.
International search report and written opinion dated Nov. 18, 2010 for PCT/US2010/049461.
International search report and written opinion dated Dec. 23, 2011 for PCT/US2011/051929.
Office action dated Apr. 3, 2014 for U.S. Appl. No. 13/232,300.
Office action dated Jul. 2, 2014 for U.S. Appl. No. 13/414,063.
Office action dated Dec. 20, 2013 for U.S. Appl. No. 13/414,063.

* cited by examiner

The EYE

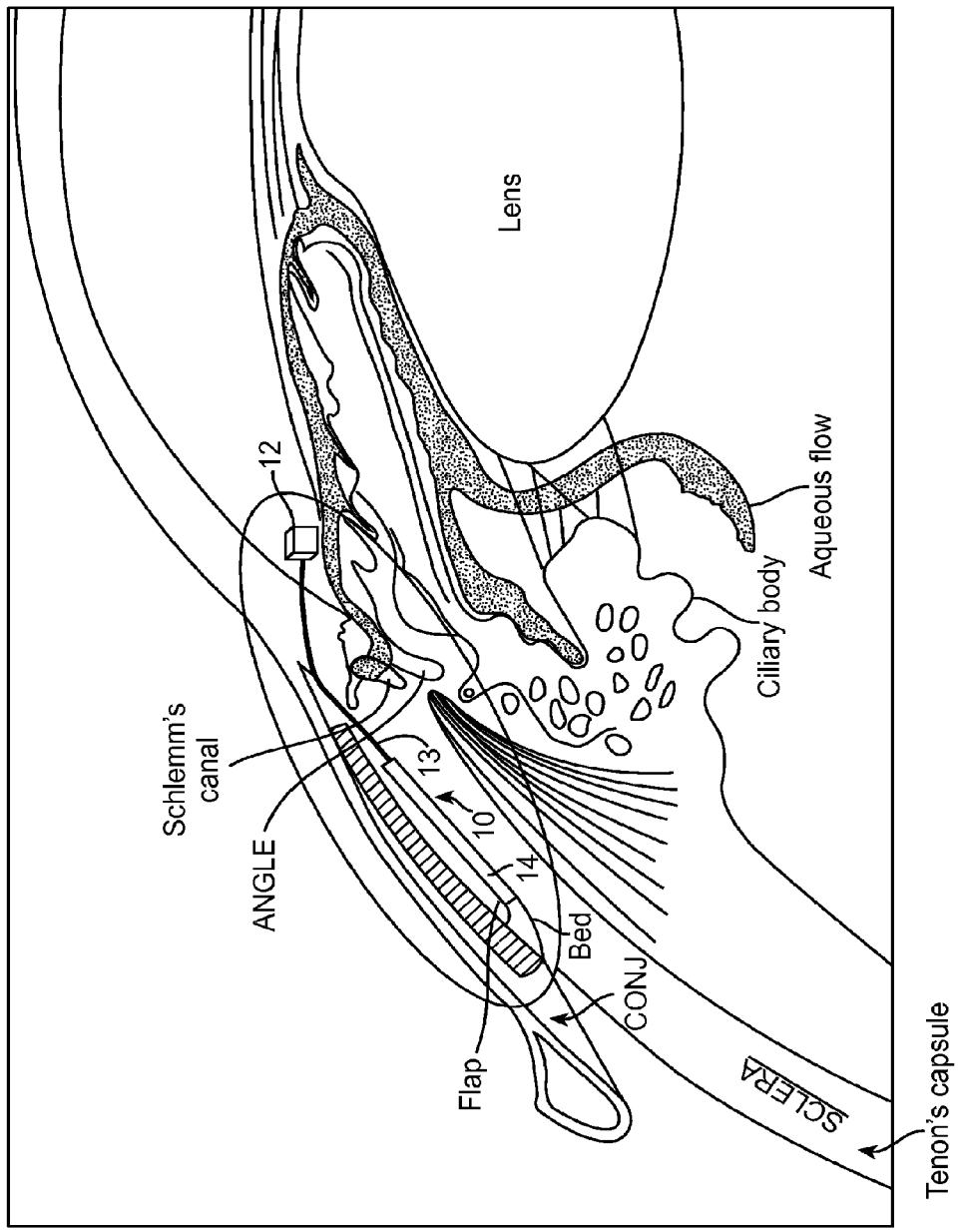
FIG. 2A1

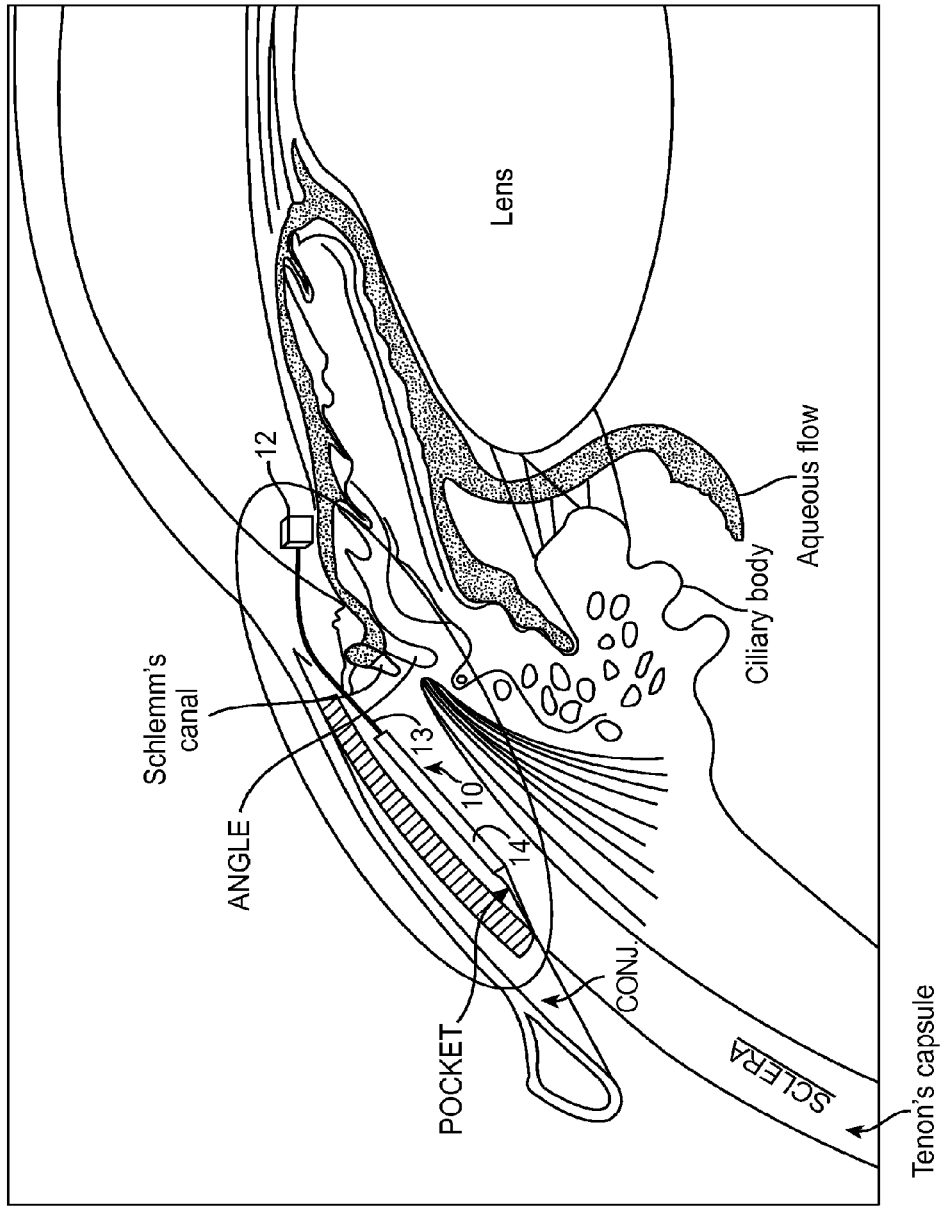
FIG. 2A2

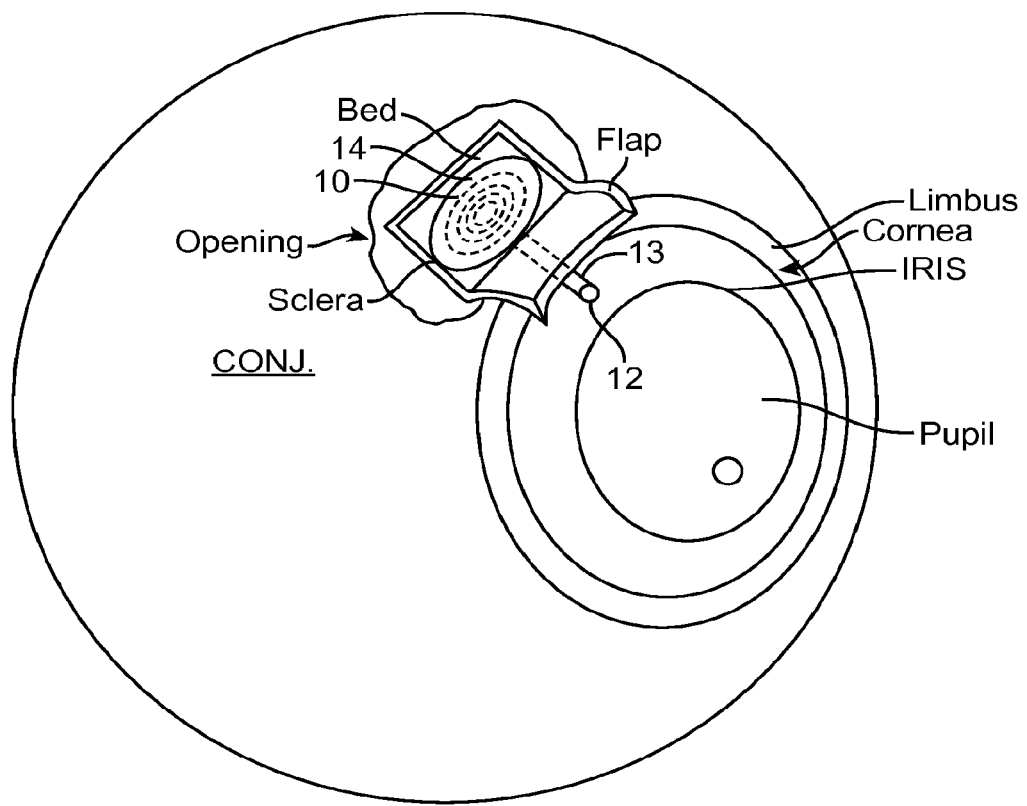
FIG. 2B1

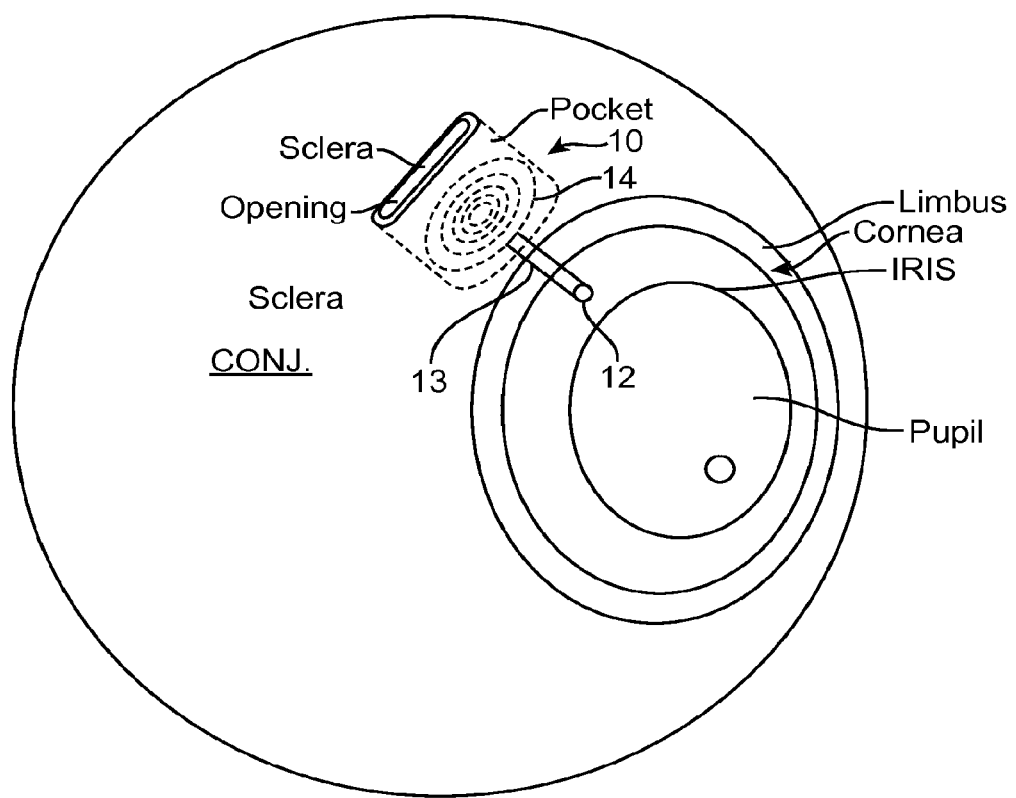
FIG. 2B2

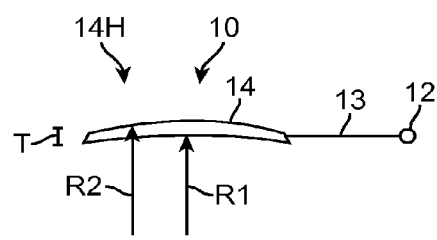
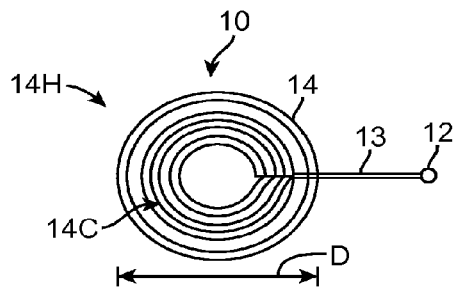
FIG. 2C  FIG. 2D
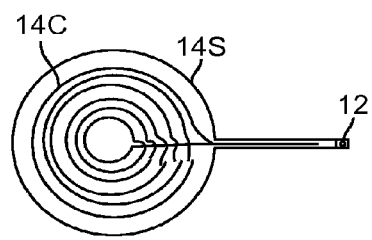
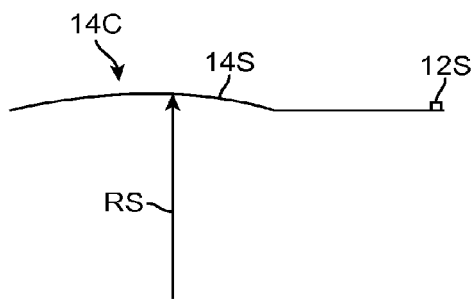
FIG. 2E  FIG. 2F
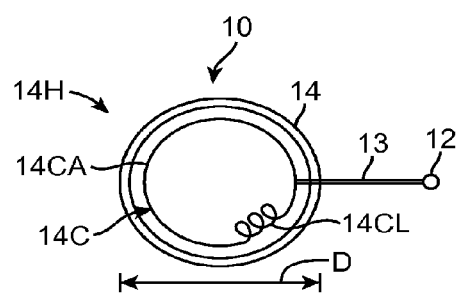
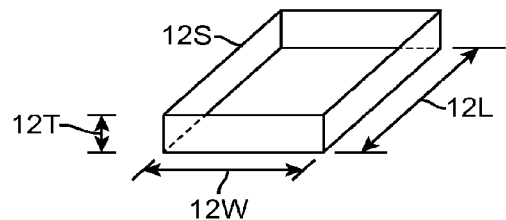
FIG. 2D1  FIG. 2G

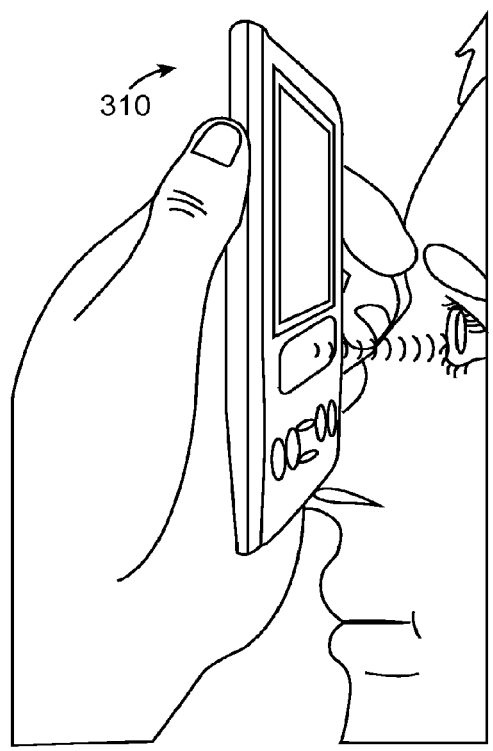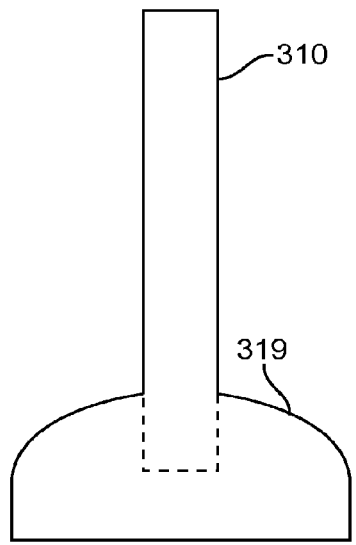
FIG. 4BFIG. 4C

500 - Method of Treating and Monitoring a Patient

- 505 - Measure patient IOP
- 510 - Determine patient has glaucoma based on IOP
- 515 - Incise conjunctiva
- 520 - Form conjunctival flap to expose sclera
- 525 - Form channel extending from conjunctiva through limbus to anterior chamber
- 530 - Provide implant to surgeon
- 535 - Position implant on sclera with distal portion extending to anterior chamber
- 540 - Suture implant to conjunctiva
- 545 - Cover implant with flap of conjunctiva
- 550 - Measure post-op IOP
- 551 - Determine geographic location of patient
- 552 - Determine atmospheric pressure at patient location
- 553 - Adjust IOP to report based on measured IOP and atmospheric pressure
- 555 - Measure IOP continuously to determine the presence of pressure spikes
- 560 - Adjust treatment based on measured IOP
- 565 - Trigger alarm in response to measured IOP above predetermined value
- 580 - Transmit the patient data from the patient measurement system to a server located remote from the patient.
- 581 - Physician prescribes target IOP for patient with physician device
- 582 - Prescribed target IOP transmitted from physician device to server or patient device for comparison with measured IOP
- 583 - Compare prescribed target IOP to measured IOP
- 584 - Notify physician with transmission to physician device when measured IOP exceeds prescribed target IOP
- 585 - Physician instructs patient based on measured IOP
    - 585A - Physician instructs patient to come into office for visit
    - 585B - Physician adjusts patient medication
    - 585C - Physician adjusts target IOP
- 589 - Analyze the data at the server
- 590 - Share data among physicians
- 591 - Patient shares data with online community
- 592 - Follow up with online patient to physician questions
- 595 - Transmit a report on the status of the patient to the treating physician
    - 595A - Transmit monthly report when IOP no more than prescribed amount
    - 595B - Transmit report daily or weekly when TOP equals or exceeds prescribed amount
- 597 - Physician issues treatment command on hand held communication device
- 599 - Repeat above steps

FIG. 5

IMPLANTABLE MEMS INTRAOCULAR PRESSURE SENSOR DEVICES AND METHODS FOR GLAUCOMA MONITORING

CROSS-REFERENCES TO RELATED APPLICATIONS

The subject application is a continuation of PCT Application No. PCT/US2010/049461 filed Sep. 20, 2010, which is related to 61/243,847 filed on Sep. 18, 2009 and 61/335,562 filed Jan. 8, 2010, both entitled "Implantable MEMs Intraocular Pressure Sensor Devices and Methods" the full disclosures of which are incorporated herein by reference in their entirety for all purposes.

BACKGROUND OF THE INVENTION

People like to see. The eye is a complex organ that allows a person to see his or her surroundings. The eye includes a cornea and crystalline lens that form an image on the retina of the eye. The retina of the eye senses the light image formed thereon and transmits neural signals via the optic nerve to the occipital cortex of the brain, such that the person can see and perceive his or her surroundings. Unfortunately, ocular diseases can compromise vision of the eye and may cause blindness in at least some instances.

Glaucoma is a major cause of blindness in the United States. In many instances, glaucoma related blindness can be prevented if caught and managed early. Glaucoma is usually associated with an increase in intraocular pressure (hereinafter "IOP"), that can result in damage to the retina of the eye. Because glaucoma is usually associated with an increase in IOP, periodic testing can be used to monitor glaucoma in order to prevent irreversible vision loss. For example, a person may undergo two to four exams per year in an ophthalmologist's office, although more examination may sometimes occur. Although treatment can be effective in many instances, in at least some patients may continue to lose vision under physician directed care. For example, about fifteen percent of patients under fifty years of age may continue to lose vision when receiving care and about thirty percent of patient over sixty may continue to lose vision.

A significant clinical need exists to detect elevated IOP such that appropriate medical and surgical treatment can be delivered to control the patient's IOP and decrease vision loss. Unfortunately, at least some of the current clinical techniques for measuring glaucoma may not detect elevated IOP, such that a patient can lose vision and may even become blind in at least some instances. For example, an ophthalmic exam may only measure IOP when the patient is in the eye clinic. In at least some instances, the patient may undergo an increase in IOP, for example a pressure spike, when the patient is away from the clinic. As such pressure spikes may not be detected, the patient may not receive treatment in time to mitigate vision loss. Further, at least some patients may not be able to visit the eye clinic on a strict regular basis, for example elderly patients and children, such that an increase in IOP may not be detected in a timely manner so as to prevent vision loss in at least some instances. Also, in at least some instances a patient may simply forget to take his or her medicine, such that the patient fails to follow the prescribed treatment.

Although measurements with an external IOP sensor can be helpful, these devices that measure pressure of the eye with an external sensor are somewhat indirect and can be inaccurate in at least some instances, such that the measured IOP may differ from the actual pressure inside the eye. In at least some instances, clinically available IOP sensors determine the IOP based on the externally measured pressure. For example, the IOP sensor can measure pressure of the eye on the external surface of the cornea, for example with applanation or indentation of the cornea. The externally sensed pressure of the eye can be used to determine the IOP of the eye based on assumptions about the anatomy and characteristics of the patient's eye. Such assumptions can lead to errors in the indirectly measured IOP when the anatomy of the patient deviates from the assumed normal anatomy and characteristics in at least some instances. For example, external IOP measurements can be affected by scleral rigidity influenced by topical anti-glaucoma drug therapy so as to induce errors in the externally measured IOP in at least some instances. As a result, in at least some instances a patient may not receive appropriate treatment.

Although implantable shunt devices have been proposed to treat IOP with drainage of the eye, many of these shunt devices are not well suited for patients with IOP that can be controlled without surgical intervention, for example medically controlled with drugs. In at least some instances, shunts may be used a last treatment option when other treatments such as medication and conventional surgery have failed. The insertion of such shunt devices can be more invasive than would be ideal, and in at least some instances shunt devices can cause the eye of the patient to be more susceptible to ocular trauma. For example, at least some shunt devices are designed to drain liquid from the eye and include a substantial chamber portion inserted into the sclera of the eye to drain liquid, such that the sclera of the eye may be weakened in at least some instances. Also, at least some of the current shunt devices can include rigid components that distort tissue and may result in ocular damage when the eye is subjected to trauma in at least some instances. Further, implanted shunt devices can migrate from an implanted location and can contribute to infection in at least some instances. Therefore, integration of a pressure sensor with a shunt device can result in an implant that is far more invasive and an eye that is more susceptible to injury than would be ideal in at least some instances.

It would be helpful to provide improved methods and apparatus that overcome at least some of the above shortcomings, for example with an implantable device capable of at least daily direct measurement of IOP in a manner that is less invasive than current devices, such that the improved device can be implanted in patients with medically controllable TOP. Ideally, such methods and apparatus can be implanted in the eye quickly and easily in an outpatient environment, and such that many patients can receive the benefit of direct monitoring of IOP.

BRIEF SUMMARY OF THE INVENTION

Embodiments of the present invention provide improved systems, devices and methods for the measurement of IOP that can be beneficial in the treatment of eyes, for example beneficial in the treatment of glaucoma. In many embodiments, an implantable device for measuring IOP comprises a distal portion, a proximal portion and a conformable elongate support extending between the distal portion and the proximal portion. The distal portion comprises a pressure sensor, for example a capacitor, and the proximal portion comprises wireless communication circuitry, for example a coil. The proximal portion is configured for placement under the conjunctiva, in many embodiments between the sclera and the conjunctiva, such that invasiveness can be decreased substantially. For example, the proximal portion may comprise an upper convex surface and a lower concave surface to retain the proximal portion between the conjunctiva and the sclera for an extended period. Also, the proximal portion may conform to the sclera and conjunctiva of the patient, for example with a combination of a soft housing and flexible materials under the housing that can be bent or flexed so as to conform the sclera and the conjunctiva. The conformable elongate support extends between the distal portion and the coil so as to couple the distal portion to the coil, and the conformable elongate support is sized to position the sensor in the anterior chamber when the proximal portion is positioned under a conjunctiva of the eye. Positioning of the pressure sensor in the anterior chamber has the benefit of providing a direct measurement of the IOP of the eye. The pressure sensor may be coated with a complaint material, such that the pressure sensor can sense pressure from a first side of the sensor and from a second side of the sensor. Such coating with a compliant material can allow the pressure sensor to measure IOP accurately with pressure from many locations of the sensor, for example along a 360 degree perimeter of the sensor and when tissue of the anterior chamber contacts one side of the pressure sensor. The conformable elongate support may be bent prior to placement of the pressure sensor in anterior chamber, such that the pressure sensor can be accurately positioned in the anterior chamber.

BRIEF DESCRIPTION OF THE DRAWINGS

FIG. 2A1 shows an implantable pressure sensor comprising a distal portion implanted in the anterior chamber to measure IOP directly, a proximal portion comprising a coil to transmit the IOP signal positioned under the conjunctiva and under a flap of sclera, and a conformable intermediate portion extending between the proximal portion and the distal portion, in accordance with embodiments of the present invention;

FIG. 2A2 shows an implantable pressure sensor comprising a distal portion implanted in the anterior chamber to measure IOP directly, a proximal portion comprising a coil to transmit the IOP signal positioned under the conjunctiva in a scleral pocket formed with blunt dissection, and a conformable intermediate portion extending between the proximal portion and the distal portion, in accordance with embodiments of the present invention;

FIG. 2B1 shows surgical placement of an implantable sensor as in FIG. 2A1 on a bed of scleral tissue with a flap of scleral tissue elevated for insertion of the sensor;

FIG. 2B2 shows surgical placement of an implantable sensor as in FIG. 2A2 in a pocket of scleral tissue;

FIG. 2C shows a side cross-sectional view of the implantable sensor as in FIGS. 2A and 2B, and the upper convex surface and the lower concave surface of the proximal portion;

FIG. 2D shows top view of the implantable sensor as in FIGS. 2A to 2C;

FIG. 2E shows top view of the thin flexible substrate of the implantable sensor as in FIGS. 2 A to 2D;

FIG. 2D1 shows top view of the implantable sensor having a coil comprising a substantially single loop antenna coupled to a second coil having a plurality of turns, in accordance with embodiments as described herein;

FIG. 2F shows side view of the thin flexible substrate of the implantable sensor as in FIGS. 2A to 2E;

FIG. 2G shows dimensions of the MEMS pressure sensor of FIGS. 2 A to 2F;

FIG. 4B shows a hand held antenna reader with components similar to the antenna reader as in 4A;

FIG. 4C shows a docking station to receive the hand held antenna reader as in 4B;

FIG. 5 shows a method of monitoring a patient, in accordance with embodiments;

DETAILED DESCRIPTION OF THE INVENTION

Figure 1A:
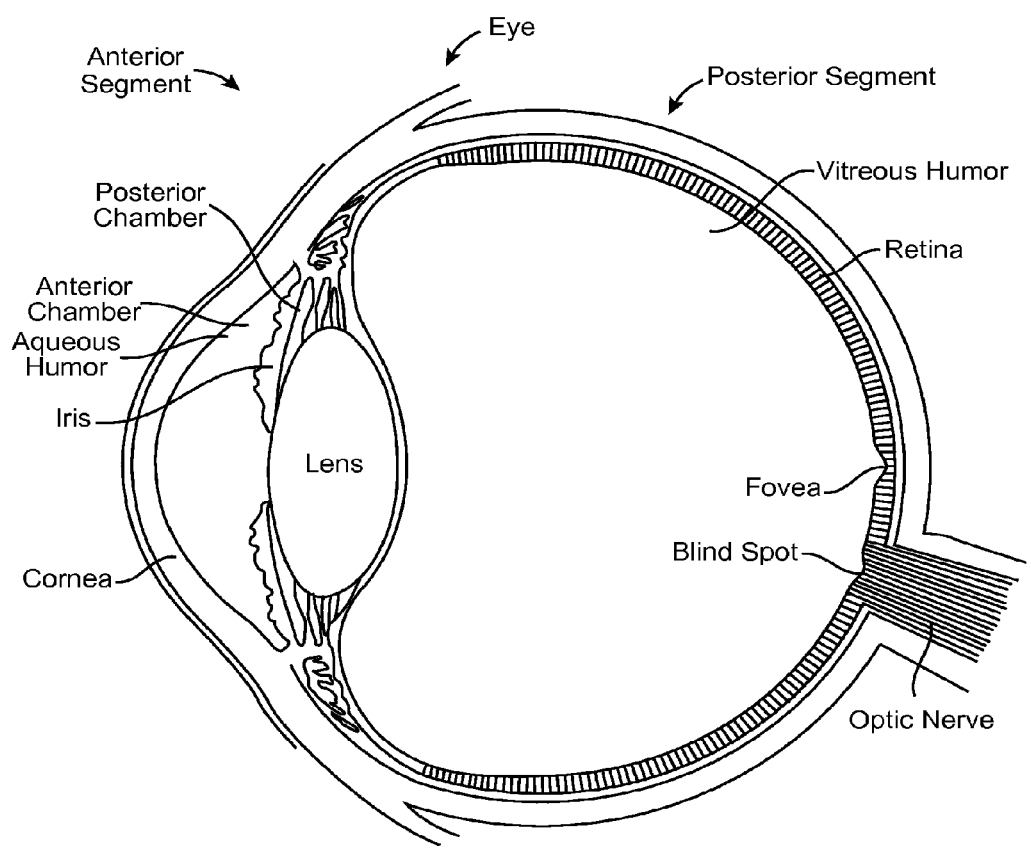
FIGS. 1A to 1C shows an eye suitable for incorporation with an implantable sensor, in accordance with embodiments of the present invention.

Embodiments of the present invention described herein can addresses a significant clinical need for glaucoma patients with medically controlled IOP, particularly those patients who may be unable to comply with a strict, regular schedule of medical treatment such as the elderly and children. Patients having glaucoma or other eye surgeries (e.g., cataract), eye injuries, certain eye tumors, or eye inflammation may also benefit from treatment with the devices and methods described herein. The construction and shape of the device allows the device to be easily implanted, thus reducing surgical time for this outpatient procedure. The implant can be temporary or permanent and is removable, and can be useful for both short term and long term monitoring of the eye. Based on the teachings described herein, the proximal portion can be configured to remain implanted between the conjunctiva and the sclera for extended time, for example one year or more. A person or ordinary skill in the art can conduct experiments to determine empirically the parameters of the implanted device, for example the thickness, curvature and conformability, such that the proximal portion can remain implanted for the extended time.

Many embodiments described herein provide a direct measurement of intraocular pressure. The intraocular pressure can be measured as often as practical, for example with a hand held reader coupled to the implanted device. The measurements can be made with sufficient frequency so as to determine the presence of diurnal IOP curves and so as to detect IOP peaks and pressure spikes. For example, the measurements can be generated hourly for the first few days following surgery, and then with decreasing frequency as the patient's pressure stabilizes. The direct IOP measurements can be made at many locations including at home or a doctor's office. The hand held device may automatically forward the patient information to the treating physician, such that the physician can monitor the patient remotely.

As used herein, the anterior segment of the eye encompasses the anterior chamber of the eye and the posterior chamber of the eye.

The implantable device component can be interrogated with an antenna and reader circuitry configured to determine IOP of the eye in response to the signal transmitted from the implanted device. The reader circuitry is coupled to a computer processor configured to a computer processor to store and transmit data.

In many embodiments, the implantable device comprises a MEMS based pressure sensor for use with the treatment of glaucoma that facilitates accurate measurement/monitoring of patient IOP in the anterior chamber. Many embodiments utilize MEMS and wireless technology that can provide direct, continuous and real-time data on IOP. The implant may comprise a spiral shaped coil joined to a pressure sensor encapsulated in a medical-grade biocompatible material. The coil can be inserted under the conjunctiva by a surgical implantation, such that the tip of the device with the attached sensor comprising the pressure responsive transducer sits inside the anterior chamber of the eye.

The implant can be removed, for example in case of adverse events.

Following implantation, direct IOP measurements can be obtained real-time and continuously with a data acquisition unit that wirelessly interrogates the implanted sensor, and includes hardware/software to control an external antenna and monitor pressure fluctuation patterns for normal/pathological conditions. The IOP measurement comprises a direct measurement as the transducer of the pressure sensor is implanted in the target tissue of interest, for example the anterior segment.

The direct IOP measurement data can be used in many beneficial ways. For example, the direct IOP measurement data can be used to trigger an alarm for the patient with the hand held reader, and the data can be transmitted to a remote server and to the office of the treating physician. The data at the remote server can be analyzed, for example mined, to determine statistical trends and analysis and algorithm development. The algorithm can be embodied in instructions of a computer program of the server. The data at the physician's office can be used by the physician to monitor the patient.

The implantable MEMS pressure sensor device and external telemetry may comprise components as described in U.S. Pat. Nos. 6,706,005, 6,682,490, and 6,447,449, the full disclosures of which are incorporated by reference and suitable for combination in accordance with some embodiments of the present invention described herein.

Figure 1B:
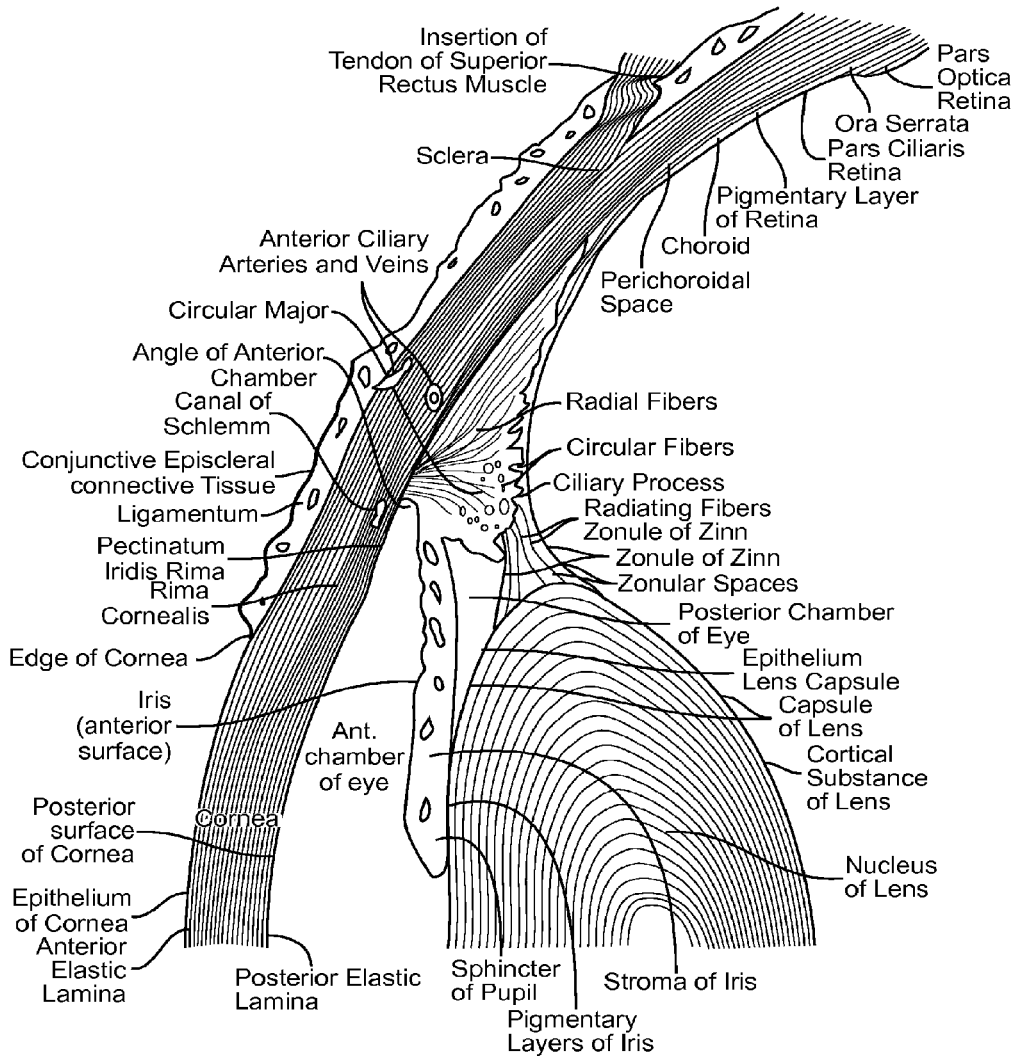
Figure 1C:
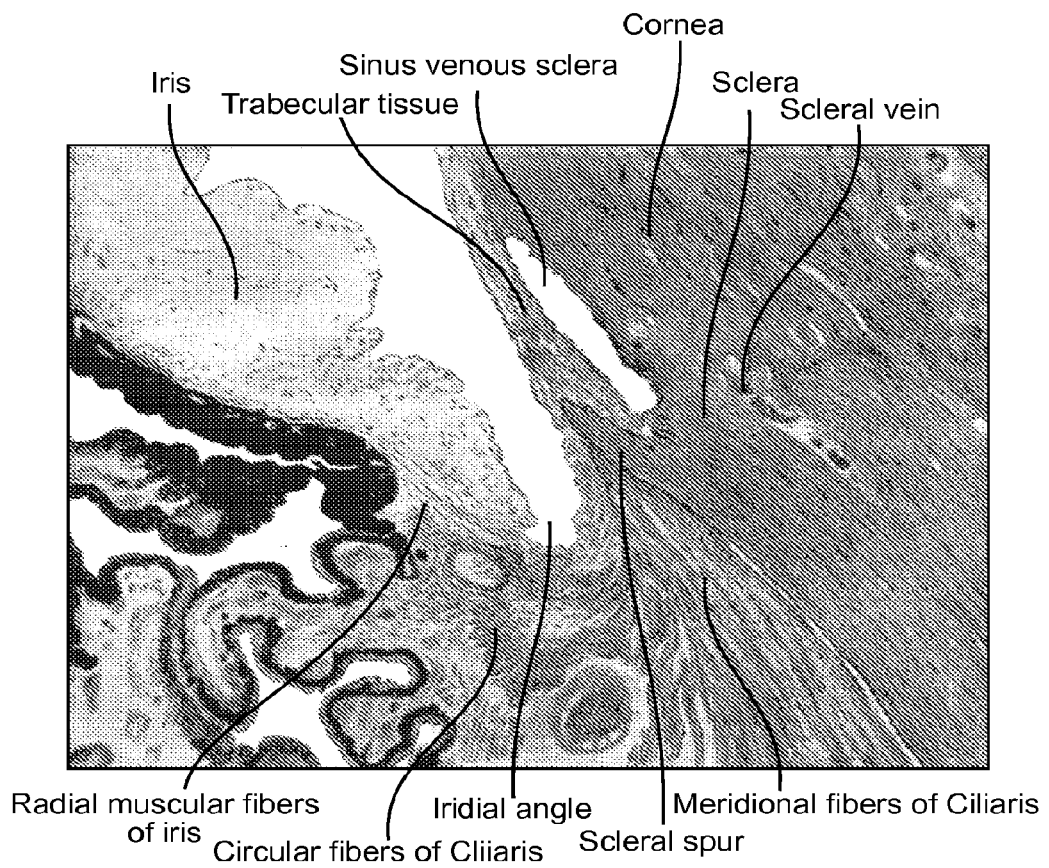

FIGS. 1A to 1C show an eye suitable for incorporation with an implantable sensor, and figures similar to FIGS. 1B and 1C can be found in Grey's Anatomy and available on the Internet, for example at the online encyclopedia Wikipedia (http://www.en.wikipedia.com). The eye comprises a cornea and lens that refract light so as to form an image on the retina of the eye. The retina comprises a fovea comprising light sensitive cones to detect light color sensitivity and high visual acuity. The retina also comprise a blind spot where the optic nerve couples to the retina. An iris is disposed over the lens and responds to light so as to dilate in darkness and constrict in bright light, such that the intensity of light striking the retina can be increased and decreased, respectively. The eye comprises an anterior segment and a posterior segment, with the lens disposed therebetween. The anterior segment comprises an aqueous humor and the posterior segment comprises a vitreous humor. The posterior chamber of the eye extends between the iris and the anterior capsule of the lens and comprises the aqueous humor. The anterior segment comprises the posterior chamber. The liquid of the eye generally drains from the posterior segment to the anterior segment and out Schlemm's canal so as to maintain intraocular pressure.

Schlemm's canal, also known as canal of Schlemm or the scleral venous sinus, comprises a circular channel in the eye that collects aqueous humor from the anterior segment and delivers the liquid of the aqueous humor into the bloodstream. The canal comprises an endothelium-lined tube. On the inside of the canal, nearest to the aqueous humor, the canal is covered by the trabecular meshwork, and this region contributes to outflow resistance of the aqueous humor.

With glaucoma, the drainage of aqueous liquid from the anterior chamber is less than ideal such that IOP can increase in the anterior chamber.

Figure 2A:
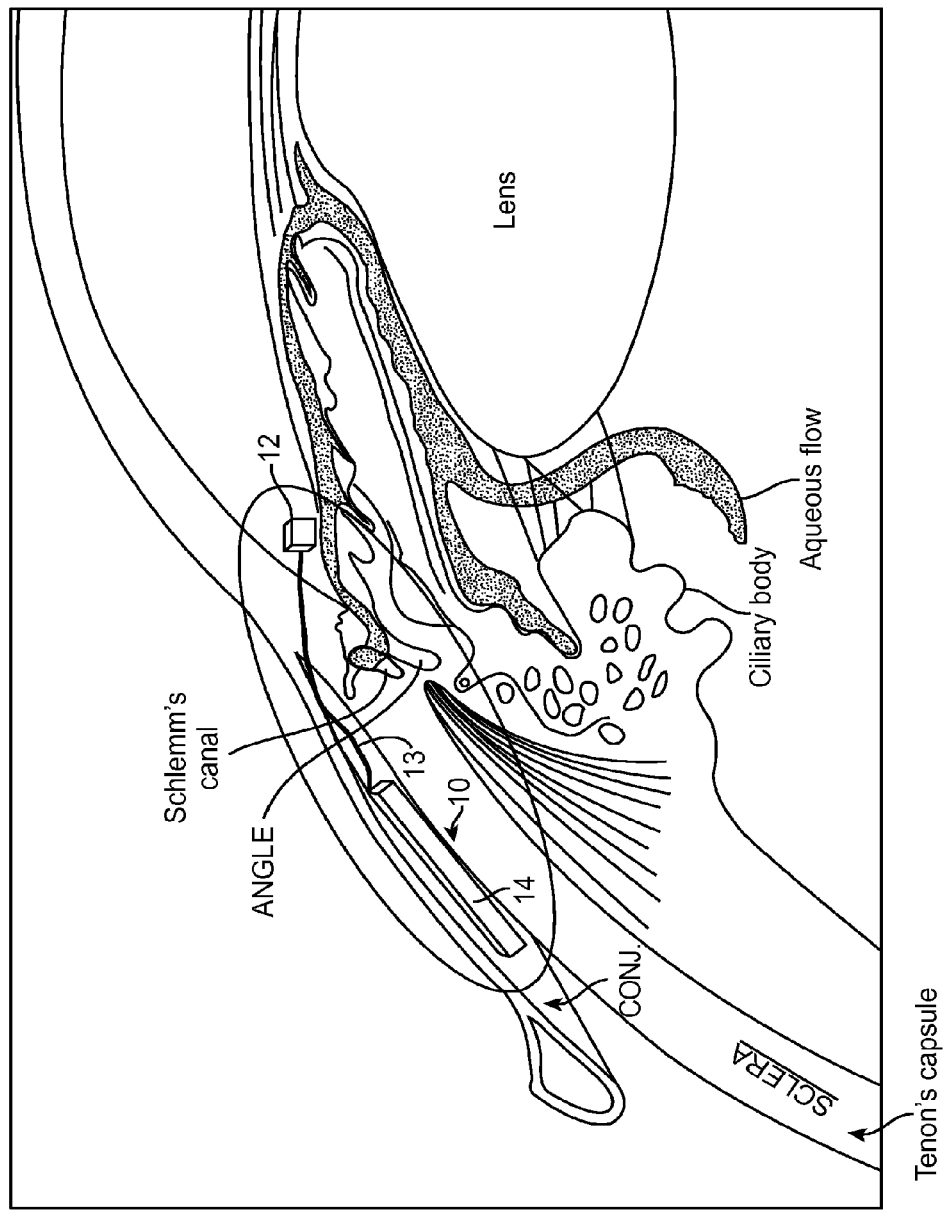
FIG. 2A shows an implantable pressure sensor comprising a distal portion implanted in the anterior chamber to measure IOP directly, a proximal portion comprising a coil to transmit the IOP signal positioned under the conjunctiva and on the sclera, and a conformable intermediate portion extending between the proximal portion and the distal portion, in accordance with embodiments of the present invention.

FIG. 2A shows an implantable pressure sensor device 10 comprising a distal portion 12 implanted in the anterior chamber to measure IOP directly, a proximal portion 14 comprising a coil to transmit the IOP signal positioned between the conjunctiva and the sclera, and a conformable intermediate portion 13 extending between the proximal portion and the distal portion. The sclera of the eye comprises Tenon's capsule disposed along a thin anterior layer of the sclera adjacent the conjunctiva, and the implant can be positioned between Tenon's capsule and the conjunctiva. Alternatively, the proximal portion may be positioned under Tenon's capsule. The implantable device may comprise a miniature, battery-less, wireless pressure sensor that can be surgically implanted with known surgical devices such as blades and sutures. The implantable sensor device may comprise transducer assembly having a capacitive pressure sensor connected to the spiral inductor to form the resonant tank circuit of the miniature wireless communication sensor device.

The proximal portion 14 can be sized and shaped in many ways for placement between the conjunctiva and sclera. For example, the housing of the proximal portion can be soft, curved and conformable, or the underlying support can be curved and conformable, or both the housing and underlying support can be curved and conformable. The proximal portion 14 comprises at least one component to transmit a signal wirelessly from under the conjunctiva to an external device such as a reader. For example, the proximal portion 14 can be sized and shaped for placement under the conjunctiva and above Tenon's capsule and the sclera. The proximal portion 14 can be conformable and shaped such that the proximal portion 14 can remain implanted under the conjunctiva for an extended time, for example one year or more, without undesirable effects such as irritation and perforation of the conjunctiva. The component to transmit a signal wirelessly may comprise many known components to transmit a signal wirelessly, such as a coil. The proximal portion 14 may comprise a conformable substrate such that the substrate and coil can bend and conform to the sclera and conjunctiva of the eye so as to minimize irritation to the eye. The coil may be coupled to the conformable substrate in many ways, for example with lithographic fabrication of the coil on the substrate or printing of the coil on the conformable substrate. The conformable substrate and coil may be coated with a biocompatible material. The proximal portion 14 may comprise an upper convex surface and a lower concave surface so as to decrease irritation of the conjunctiva and sclera.

The coil can be fabricated on substrate, which together may form a structure that corresponds to the curvature of the eye. The structure that corresponds to the curvature of the eye may comprise many shapes such as spherical or elliptical, and the structure may conform to the curvature of the eye. The proximal portion comprising the structure can be inserted in the eye in an incision made to the conjunctiva and sutured to the sclera. The longest dimension across the curved structure, for the example the diameter, can be no more than about 15 mm, and a thickness T of the plate may be no more than about 1 mm. The dimensions can be smaller and the diameter of the proximal portion can be no more than about 10 mm, for example 6 mm, and the thickness can be no more than about 0.5 mm, for example about 0.3 mm. Based on the teachings described herein, a person of ordinary skill in the art can conduct experiments to determine empirically the diameter and thickness of the proximal portion to implant the sensor device for an extended period of at least one year.

The distal portion 12 comprises a pressure sensor to measure directly pressure of the anterior chamber of the eye. The pressure sensor 12 may comprise many known pressure sensors, for example a piezoelectric diaphragm or a capacitor, or a combination thereof. The pressure sensor 12 may comprise a compliant material positioned over the sensor such that sensor can measure pressure from many locations of the sensor such as along a 360 degree perimeter and each of a first side of the sensor and a second side of the sensor. This sensitivity to pressure on each of the first side and the second side can be helpful as the sensor can accurately measure IOP when the pressure sensor contacts tissues when implanted in the anterior chamber, for example at least one of the cornea or the iris. Although the pressure sensor 12 may comprise many cross-sectional sizes, in many embodiments, the pressure sensor comprises a cross sectional size of no more than about 1 mm across such that the pressure sensor can be inserted into the anterior chamber, for example a cross sectional size of no more than 0.5 mm such as 0.3 mm. The distal portion can be passed through the limbus with a tunnel, or channel, having a dimension across, for example a diameter across, of no more than about 1 mm, for example no more than 0.5 mm such as 0.3 mm. The pressure sensor may comprise many types of pressure sensors of suitable size and biocompatibility for use in accordance with the embodiments described herein.

The conformable intermediate portion 13 can be configured to conform to the eye in many ways. The conformable portion 18 may comprise material that can bend or flex when the eye is subjected to trauma, so as to decrease trauma to the eye for example when the eye is struck with an object. For example, the conformable portion may comprise a flexible substrate with electrical traces printed thereon an a complaint material positioned over the traces and substrate. Alternatively or in combination, the pressure sensor can be located at the distal tip of a flexible tube comprising wires that electrically connects the sensor to the coil. The tube can be tunneled through the limbus and into the anterior chamber for direct measurement of IOP. The tube may comprise a cross-sectional size from about 1 to 3 French, and can be approximately 10 mm in length. The tip or distal portion of the tube may be bent to a prescribed curve for accurate positioning in the anterior chamber. For example, the prescribed curve may correspond to a curvature of the eye, such as the curvature of the eye extending between the sclera and limbus. The intermediate portion may comprise a length suitable for placement of the sensor at a desired distance into the anterior chamber, for example about 1.0 to 1.5 mm, although other distances may be used.

Figure 2B:
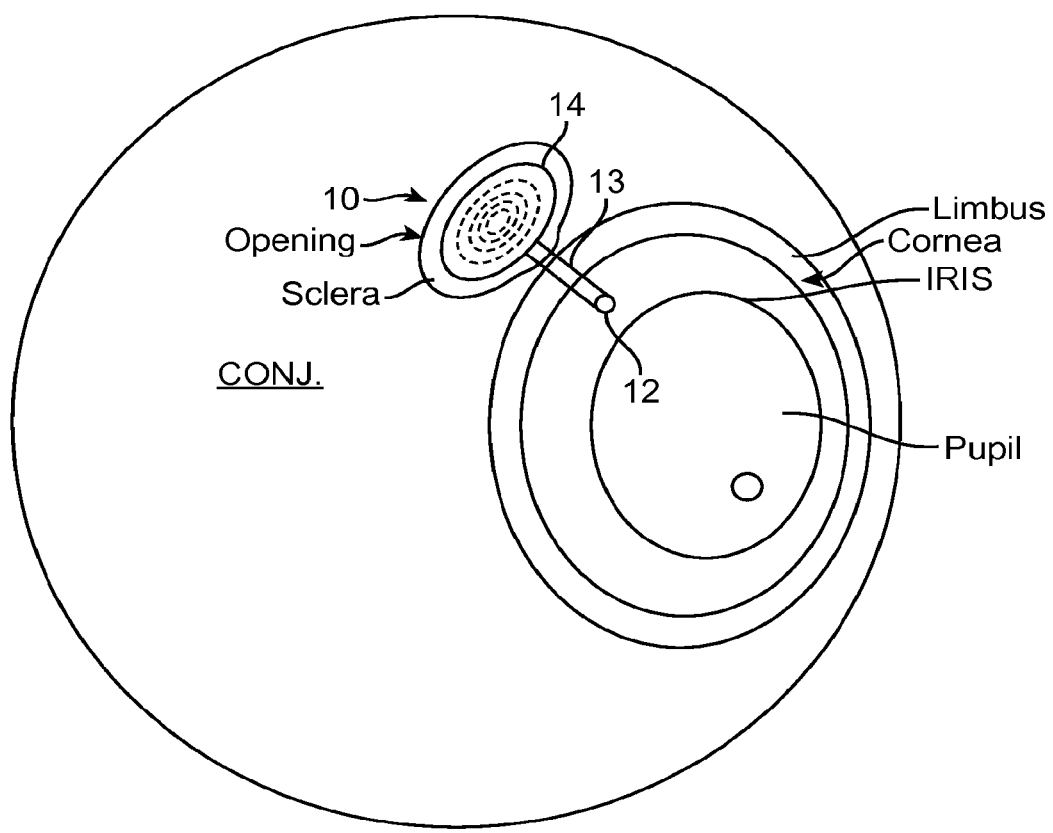
FIG. 2B shows surgical placement of an implantable sensor as in FIG. 2A through an opening in the conjunctiva such that the sensor is positioned under the conjunctiva.

FIG. 2B shows surgical placement of an implantable sensor as in FIG. 2A into an opening in the conjunctiva. An incision is made in the conjunctiva proximal and posterior to the limbus so as to form an opening to access the sclera. The proximal portion comprising the curved substrate and coil is inserted through this incision and positioned beneath the conjunctiva and on top of the sclera and Tenon's capsule. The proximal portion 14 comprising the curved substrate and coil can then be sutured to the sclera with suture holes. A channel, or tunnel, can be created that extends from the conjunctiva to the anterior chamber, and the intermediate portion 13 tunneled into the limbus such that the distal portion 13 comprising the sensing tip extends into the anterior chamber of the eye. The components of the implant comprising the proximal portion, the distal portion, and the elongate support can be slid into position together, such that the procedure can be performed quickly and with accurate placement of the transducer in the anterior chamber and accurate placement of the proximal portion. The distal portion and at least a portion of the elongate support can be passed through the incision, and the distal portion passed through the limbus when the proximal portion is inserted into position through the incision in the conjunctiva, such that the distal portion is positioned in the anterior chamber when the proximal portion is positioned on the sclera. The packaging of the proximal portion may comprise fenestrations sized to receive sutures so as to anchor the implantable device, and the proximal portion may be sutured to the sclera. The conjunctiva is sutured closed.

FIG. 2A1 shows implantable pressure sensor 10 comprising a distal portion implanted in the anterior chamber to measure IOP directly, a proximal portion comprising a coil to transmit the IOP signal positioned under the conjunctiva and under a flap of sclera, and a conformable intermediate portion extending between the proximal portion and the distal portion. The sensor is positioned on the bed. The flap of scleral tissue is shown positioned over the sensor.

FIG. 2B1 shows surgical placement of an implantable sensor as in FIG. 2A1 on a bed of scleral tissue with a flap of scleral tissue elevated for insertion of the sensor. The flap of scleral tissue can be cut and lifted to expose a scleral bed sized to receive the implantable sensor 10. A small incision can be formed from the bed to the anterior chamber, which incision is sized to receive the intermediate portion 13 and pressure sensor 12. The implantable sensor can extend from the scleral bed to the anterior chamber where the pressure transducer element is located for direct measurement of IOP. The flap of scleral tissue can be positioned over the proximal portion 14 of sensor 10, and the flap may be sutured in place. The flap of scleral tissue can cover the sensor to decrease visibility of the sensor, so as to provide cosmetic benefit to the user. The flap can also fix the position of the sensor, for example when the flap is sutured in position.

FIG. 2A2 shows an implantable pressure sensor 10 comprising a distal portion having a pressure sensor 12 implanted in the anterior chamber to measure IOP directly with sensor 12. A proximal portion 14 comprises a coil to transmit the IOP signal. The proximal portion 14 is positioned under the conjunctiva in a scleral pocket. The pocket can be formed in many ways, for example with blunt dissection. The conformable intermediate portion 13 extends between the proximal portion 14 positioned in the pocket and the distal portion comprising sensor 12 positioned in the anterior chamber.

FIG. 2B2 shows surgical placement of an implantable sensor as in FIG. 2A2 in a pocket of scleral tissue. An opening can be formed in the conjunctiva, and an incision is made the sclera to the intended depth of the pocket. A blunt dissection instrument can be passed through the opening to separate layers of sclera and form the pocket. The pocket is sized to receive the proximal portion 14. A small tunneling incision can be made that extends from the pocket to the anterior chamber to receive the proximal portion 13 and the distal portion comprising pressure sensor 12. The sensor 10 can then be inserted into the pocket distal end first and advanced to the final intended position with the distal portion comprising pressure sensor 12 at least partially located in the anterior chamber to measure IOP directly. When the sensor is positioned, the opening can be closed, for example with sutures. The pocket of scleral tissue can cover the sensor to decrease visibility of the sensor, so as to provide cosmetic benefit to the user. The pocket can also fix the position of the sensor, for example when the opening to the pocket is sutured in position.

FIG. 2C shows a side cross-sectional view of the implantable sensor 10 and the upper convex surface and the lower concave surface of the proximal portion, and FIG. 2D shows top view of the implantable sensor. The implantable sensor 10 comprises a soft housing 14H, for example a silicone elastomer, disposed around the coil 14C. The lower concave surface of the proximal portion 14 comprising housing 14H may comprise a spherical concave surface having a radius of curvature R1. The upper convex surface of the proximal portion 14 comprising housing 14H may comprise a spherical convex surface having a radius of curvature R2. The proximal portion 14 may comprises a substantially uniform thickness T extending across a majority of the proximal portion. The first radius of curvature R1 and the second radius of curvature R2 may correspond substantially to a spherical radius of curvature of the eye, for example a radius of curvature of the eye where the implant is positioned such as along the interface of the sclera and the conjunctiva. At least the housing 14H comprises the lower spherical concave surface corresponding to the first radius of curvature R1 and the upper spherical convex surface corresponding to the second radius of curvature R2. Although the coil 14C can be substantially flat and disposed substantially along a plane with the housing curved with the upper and lower curved surfaces, the coil 14C will often comprise a spherically curved shape corresponding to the upper and lower curved surfaces of the housing 14H, such that the proximal portion 14 may comprise a thin profile suitable for placement for an extended period, for example positioned above Tenon's capsule and under the sclera for at least one year. The curved coil may be formed in many ways, for example printed on a curved substrate.

The proximal portion 14 may comprise a maximum distance across, for example diameter D, that can be sized in many ways such that the proximal portion can be positioned under the conjunctiva for an extended period. For example, the diameter D may comprise no more than about 15 mm across, for example no more than about 10 mm across, such that the implant can be retained between the conjunctiva and the sclera for an extended time. The diameter D may comprise a smaller size, for example no more than about 6 mm across. The substantially uniform thickness T extending across a majority of the proximal portion 14 can be sized in many ways, and may comprise no more than about 1 mm, for example no more than about 0.5 mm. A person of ordinary skill in the art can determine empirically the size of the diameter D and thickness T, based on the teachings described herein, such that the proximal portion can be positioned at a target tissue location for an extended period, for example between the sclera and conjunctiva for an extended period of at least one year.

FIG. 2G shows dimensions of pressure sensor 12S of the distal portion 12. The pressure sensor 12S may be fabricated on the same substrate as the coil, or can be separate and attached to the coil. Pressure sensor 12S comprises a transducer to convert pressure to an electrical signal, for example with capacitance. The pressure sensor 12S comprises a length 12L, a width 12W and a thickness 12T. The thickness 12T may comprise no more than about 0.5 mm, for example 0.4 mm or less, such that the compliant coating can be positioned over the sensor and the resulting coated sensor suited for placement in the anterior chamber. The length 12L and the width 12W may comprise many sizes such that the sensor is suited for placement in the anterior chamber, for example about 0.7 mm square with a surface area of about 0.5 mm$^2$. The length 12L and width 12W may correspond to many geometries such as rectangles and squares. The sensor 12S may comprise may shapes, for example non-rectangular shapes such as circular, hexagonal or triangular.

FIG. 2D1 shows top view of the implantable sensor 10 having coil 14C comprising a substantially single loop antenna MCA coupled to a second coil 14CL having a plurality of turns. Second coil 14CL may comprise an inductor such as a toroidal coil, for example. The second coil 14CL may comprise a coil of the MEM circuitry formed on the substrate as described herein.

FIG. 2E shows top view of the thin flexible substrate 14S of the implantable sensor and FIG. 2F shows side view of the thin flexible substrate 14S of the implantable sensor. The thin flexible substrate may comprise a spherically curved surface that corresponds to a radius RS of curvature of the substrate, similar to first radius of curvature R1 and second radius of curvature R2. The curved thin flexible substrate 14S allows the thickness of the curved proximal portion 14 to be curved and have a thinner profile, for example thinner than a flat substrate. The soft housing 14H and thin flexible substrate can be combined such that the proximal portion 14 comprising a highly conformable portion well suited for safe placement for an extended period.

For example, a flexible substrate 14S, or support, may comprise an outer boundary profile corresponding substantially to the shape of the implant as seen in FIG. 2D. The flexible substrate 14S can support each of the coil 14C of the proximal portion, the pressure sensor 12S of the distal portion, and traces of conductive material extending between the coil and the pressure sensor, such that the implant and flex and/or bend with the eye. The curved, thin flexible substrate may comprise a curved flexible printed circuitry board material with the coil printed thereon, and traces extending to the pressure sensing transducer printed thereon. The pressure sensor 12S comprising the transducer, for example a MEMS capacitor chip, may comprise a component positioned on the distal portion of thin flexible substrate 14S and affixed thereto.

The coil 14C comprising a substantially single loop antenna 14CA coupled to a second coil 14CL having a plurality of turns can be located on the substrate 14S. The second coil 14CL comprising the inductor can be placed on the support 14S with pads and traces to couple to the coil.

System Components and Function

Figure 3:
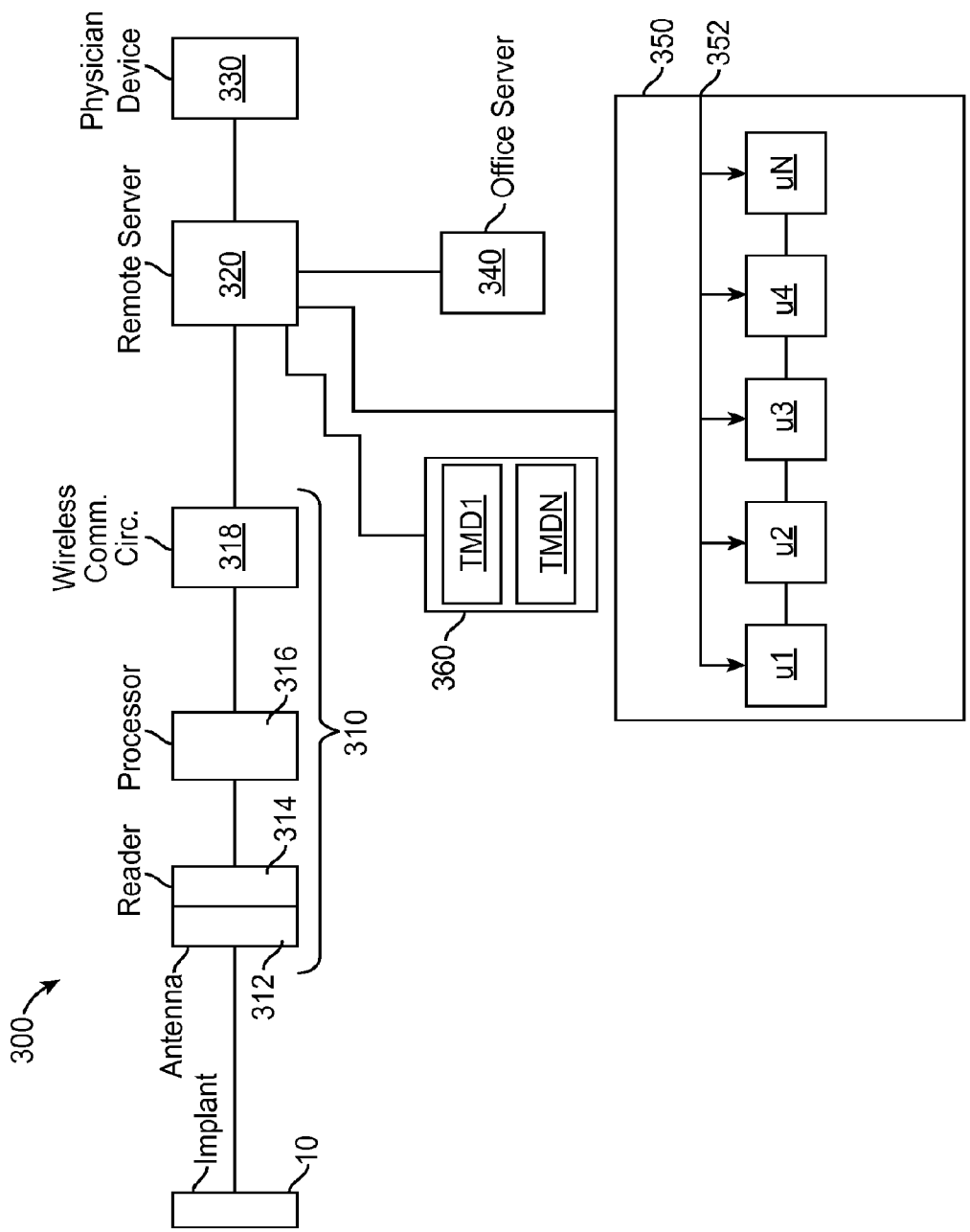
FIG. 3 shows components of a telemetry system comprising the implantable sensor, in accordance with embodiments.

FIG. 3 shows components of a telemetry system 300 comprising the implantable sensor. The wireless communication based pressure sensing system may comprise several components. The implantable sensor 10 is configured to couple to an external reader 310, for example an antenna/reader, to determine the resonant frequency of the pressure sensitive capacitor and inductor circuit. The antenna/reader comprises an antenna 312 and reader circuitry 314 to determine the resonant frequency of the implanted sensor. The external reader 310 is configured to determine the patient IOP based on the directly measured pressure within the eye and the external atmospheric pressure. As atmospheric pressure can fluctuate approximately +/−10 mm of Hg and may also change with the elevation of the patient, the accuracy of the patient IOP reported to the physician and patient can be improved substantially by determining the reported IOP based on the IOP measured directly with the implanted pressure sensor and the atmospheric pressure external to the eye.

The external reader 310 can be configured in many ways to determine the IOP of the patient based on the directly measured IOP and the atmospheric pressure. For example, the external reader 310 may comprise an atmospheric pressure sensor to determine the IOP reported to the physician and the patient based on the IOP measured directly with implanted sensor and the local atmospheric pressure. Alternatively or in combination, the external reader 310 may have two way communication with an external weather site to determine the atmospheric pressure from the external site. For example, the external site may comprise a local weather station or web site having a corresponding internet address, and the atmospheric pressure where the patient is located can be determined based on one more of postal zip code, latitude and longitude, or global positioning system coordinates. The external reader 310 may comprise circuitry to determine the location of the patient and use the patient position in formation to determine the pressure where the patient is located based on meteorological weather information. The global positioning coordinates of the patient can be determined in many ways, for example with location based on a cellular phone connection of the external reader 310 or based on GPS circuitry of the reader 310.

Atmospheric pressure associated with weather can fluctuate slowly and on the order of +/−about 10 mm of Hg, such that correction of measured patient IOP based on commercially available meteorological information can be sufficient to provide accurate determination of the patient IOP when combined with the directly measured IOP. Also, by determining the location of the patient, fluctuations in atmospheric pressure associated with the elevation where the patient is located can determined and used to determine the patient IOP. For example, the IOP reported to the physician and patient can be determined by subtracting the barometric pressure at the location and elevation of the patient from the directly measured IOP to determine the corrected IOP reported to the physician and patient. The elevation of the patient can be determined based on the location of the patient, for example when the patient is located at a city near sea level or a city in the mountains. The rate of change in patient location can also be used, for example when the patient flies and location changes quickly.

The adjusted IOP (AIOP) for patient reporting and can be determined in many ways based on the directly measured internal IOP and externally measured atmospheric pressure. For example, the adjusted IOP (ΔIOP) may comprise a differential IOP determined by subtracting the external atmospheric pressure (ATP) from the internally measured IOP (IMIOP) with the equation (AIOP)=(ΔIOP)=(IMIOP)−(ATP).

Although a calculation is shown, the adjusted IOP can be determined in many ways, for example with a look up table stored in a processor.

The antenna/reader is coupled to a processor 316 comprising a computer readable medium having instructions of a computer program embodied to determine the intraocular pressure, for example with a look up table, in response to the resonant frequency and the local atmospheric pressure. The at least one processor can be coupled to the Internet with wired or with wireless communication circuitry and transmit the patient data to a server 320 located remote from the patient. Alternatively or in combination, the patient data can be transmitted to a treating physician for evaluation of the patient. For example, the data can be transmitted to a server located at the treating physicians office. The data can also be transmitted to the physician with wireless cellular communication, for example to a handheld physician communication device such as a pager, iPhone™, Blackberry™, such that the physician can evaluate the status of the patient and may adjust treatment of the patient accordingly.

The external antenna/reader 310 may comprise a handheld ambulatory device comprising the atmospheric pressure sensor, the processor 316 and the wireless communication circuitry such that the patient can transmit measurement data with the wireless communication circuitry. For example, the wireless communication circuitry may comprise one or more of Wi-Fi circuitry or cellular circuitry, such that the patient user can measure and transmit data to the central server when the patient is mobile. The handheld ambulatory external reader 310 may comprise circuitry similar to hand held communication devices such as pagers and smart phones, for example the iPhone™ or the Blackberry™ smart phones. The handheld external reader 310 may comprise instructions of a computer readable program embodied on a tangible medium to determine the IOP reported to the physician based on the IOP measured directly with implanted sensor and the atmospheric pressure. For example, the atmospheric pressure can be determined based on the location and elevation of the patient and local barometric pressure, as described herein.

The remote server 320 may comprise data from many patients and comprise instructions of a computer program embodied on a programmable memory, such that the data from many patients can be combined and analyzed. For example, the server may comprise a data center where data are analyzed and physicians can share patient data. Alternatively or in combination, the patient data can be transmitted to a treating physician for evaluation of the patient. For example, the data can be transmitted to a server 340 located at the treating physicians office. The data can also be transmitted to the physician with wireless cellular communication, for example with to a handheld physician communication device 330 such as a pager, iPhone™ smart phone, or Blackberry™ smart phone, such that the physician can evaluate the status of the patient and may adjust treatment of the patient accordingly.

The system 300 may comprise a processor system, and the processor system may comprise two or more of the processor located with the patient, the remote server, the server located at the physician office, and the hand held physician communication device. The remote server comprises processor comprising a computer readable medium having instructions of a computer program embodied thereon so as to store patient data with a database.

The hand held communication device 330 can be configured such that the physician can transmit treatment instructions for patient treatment so as to close the loop of the treatment for the patient, for example with changes to medication or requesting a patient examination. The remote server, comprises processor comprising a computer readable medium having instructions of a computer program embodied thereon so as to store patient data with a database. The remote server may also forward treatment instructions from the physician device 330 to the patient device 310.

The instructions from the handheld physician communication device allow the physician to direct patient treatment. For example, the physician can instruct the patient to come in for a visit, for example to assess the status of the patient need for additional surgical intervention. The physician may adjust the patient medication, for example increase the patient medication. The physician may set a target IOP for the patient based on the clinical assessment of the patient. Some patient who have lost vision can be more sensitive to IOP than those who have not, such that the physician may set the target IOP for a patient with vision loss lower than a patient who has not lost vision. For example, the physician can set the target IOP for a patient with vision loss at 12 mm Hg, and the target IOP for a patient with no vision loss at 21 mm Hg. The physician assessment of patient vision loss can be determined in many ways, for example with one or more of visual fields testing or the cup to disk ratio which is known measurement to assess the progression of glaucoma. The above treatment instructions may comprise menu selections of hand held physician device 330 that can be selected and forwarded to the hand held patient reader device 310.

The handheld communication device 330 may comprise a processor comprising a computer readable medium having instructions of a computer program embodied thereon so as to store and display patient data for diagnosis and treatment, for example data received from the server. The server located at the physician office may comprise a processor comprising a computer readable medium having instructions of a computer program embodied thereon so as to store patient data with the database. The remote server may comprise the server at the physician office.

The remote server 320 can be configured to communicate with processors of a community 350 of online users. The community 350 of online users may comprise a plurality of processors 352. The plurality of processors 352 may comprise, for example, a first user processor U1 of a first user, a second user processor U2 of a second user, a third user processor U3 of a third user and a fourth user processor U4 of a fourth user and an Nth user processor UN of an Nth user, for example a one millionth user. The online community 350 may comprise patients monitored with the implanted sensor device and friends, family members and care givers of the patients. The community of user may be connected with an online community social networking site comprising a virtual community. For example the online community may comprise Facebook users.

The remote server 320 can be coupled to a community of remote online physicians 360 who can compare data and who can provide telemedecine to members of the online community 350. The community of remote online physicians can practice telemedecine with a patient, for example a patient of the community of users. The treating physician and physician device 330 may comprise a member of the community of remote online physicians 360. Each physician has access to a processor comprising a tangible medium having computer readible instructoins stored thereon, for example a smartphone, a tablet computer, a notebook computer or a desk compuer. For example a first processor TMD1 comprising a smart phone may be used by a first physician and a second processor TMD2 comprising a notebook computer may be used by a second physician.

The remote server 320 can control communication and access of the patient data, and may be configured to display information on the displays of the online community 350 and the processors of the community of remote online physicians. The remote server 320 can receive commands from the physician and transmit the treatment commands to the hand held external reader 310. For example, the physician can prescribe a target IOP for the patient based on the physician's evaluation of the patient, and the customized physician prescribed target IOP can be transmitted to the hand held external reader 310. The handheld external reader may comprise instructions of a computer program such that a message is transmitted to the treating physician, for example an email, when the patient IOP exceeds the customized prescribed target IOP. Alternatively or in combination, the remoter server may comprise instructions to transmit a message to the physician when the patient IOP exceeds the physician prescribed IOP for the patient.

Wireless Pressure Sensor.

Figure 3A:
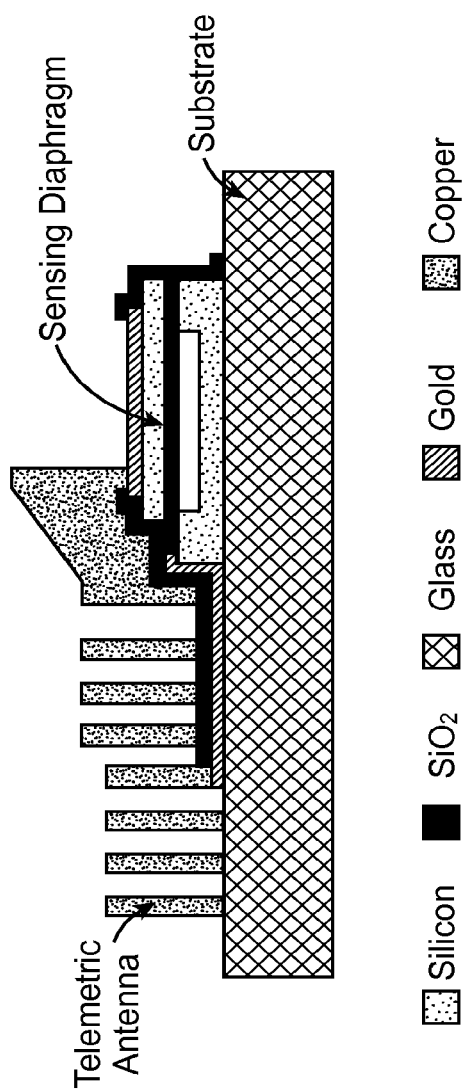
FIG. 3A shows components of an implantable sensor as in FIGS. 2A and 2B, in accordance with embodiments of the present invention.

FIG. 3A shows components of an implantable pressure sensor as in FIGS. 2A to 2D. The capacitive pressure sensor is connected to the spiral inductor to create the LC resonant tank circuit of the miniature wireless sensor.

The pressure sensors may comprise many of types of known biocompatible pressure sensors sized for placement in the anterior chamber.

The pressure transducer assembly 240 may comprise a micro-electro-mechanical system (MEMS) and can be fabricated with known methods. The coil may be fabricated on the same substrate as the pressure sensor (1-chip). Alternatively the coil can be fabricated on a first substrate separate and the pressure sensor fabricated on a second substrate, and the coil coupled to the pressure sensor (2-chip). The coil can be coupled to the pressure sensor in many ways. For example, the pressure sensor can be joined or attached to the coil with wires or with traces on a common substrate such as a flex printed circuitry board, so as to comprise a MEMS/fiex PCB hybrid device. The pressure sensor may comprise a single chip sensor supported with a substrate, for example glass. The pressure sensor and substrate may be positioned on a flexible support having traces as descried above. For example, the traces may comprise the substantially single loop antenna coupled to the second inductor having the plurality of turns as described above.

The pressure sensor may comprise a plurality of layers deposited on the substrate. A layer of conductive silicon semiconductor can be deposited on the glass substrate and shaped with lithography and etching so as to form a lower side of the capacitor. A layer of gold can be deposited over the silicon and glass so as to form a lead extending from the lower side of the capacitor to the center of the coil. A dielectric layer, for example $SiO_2$, can be deposited over the gold to insulate the antenna from the lead and separate the lower side of the capacitor from the upper side. A layer of conductive silicon semiconductor can be deposited on the dielectric layer opposite the lower side of the capacitor and shaped to form the upper side of the capacitor. The upper side of the capacitor may comprise a sensing diaphragm that bends with pressure so as to decrease spacing of the first side of the capacitor from the second side such that the capacitance increases when pressure increases. A layer of conductor, for example gold, can be deposited on the second side of the capacitor comprising the pressure sensing diaphragm, and the conductor can be shaped to couple to the coil comprising the telemetric antenna. A conductor, for example copper, can be deposited at least partially over the dielectric layer and sensing diaphragm such that the lower side of the capacitor is coupled to the inner portion of the coil and the upper portion of the capacitor comprising the sensing diaphragm is coupled to the outer portion of the coil.

As noted herein, the coil may comprise the substantially single loop coil antenna and the second coil having the plurality of turns. The layer of conductor deposited on the substrate may be shaped so as to comprise one or more of the single loop telemetric antenna 14CA or the second inductive coil 14CL.

The pressure sensor may be calibrated for the elevation of the location where the patient lives, and can have an average pressure and frequency corresponding to the pressure at the elevation where the patient lives.

Packaging.

Figure 3B:
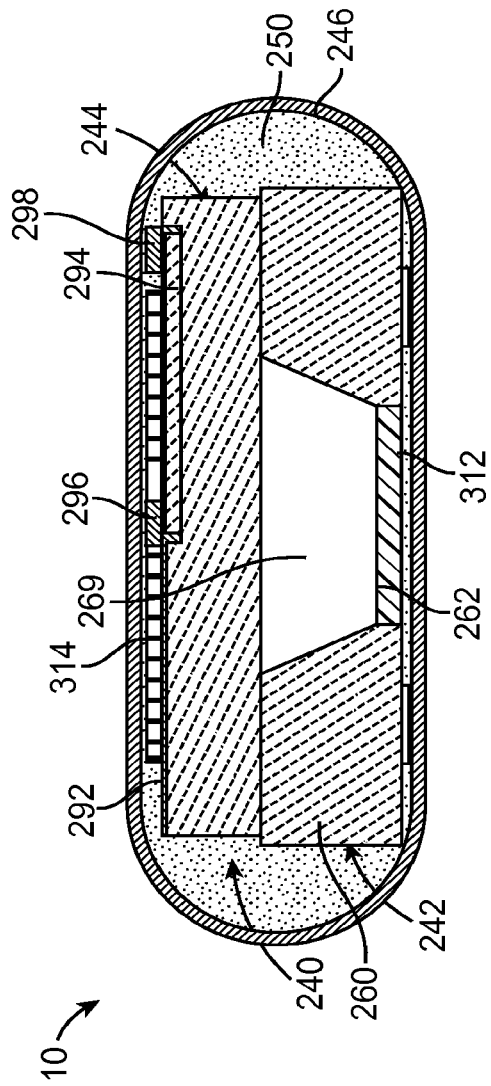
FIG. 3B shows a cross-sectional view of packaging of an implantable sensor, in accordance with embodiments of the present invention.

FIG. 3B shows a cross-sectional view of packaging of implantable pressure sensor 10. To protect the MEMS pressure sensor with wireless telemetry from corrosion, the implant device may be coated or encapsulated in a soft biocompatible polymer such as polydimethylsiloxane (PDMS). The sensor can read pressure from all directions as a result of its compliant enclosure 246, which is filled with a conformable material 250 such as liquid, viscous material, or gel (e.g., silicone, saline or other biocompatible material). This allows pressure to be uniformly exerted on the pressure sensor 212, such that pressure can be sensed from forces on a side opposite the pressure sensor. For example, the implant can be positioned such that the pressure sensor is located on a first side of the implant opposite a second side of the implant, and the device can measure pressure of the anterior chamber when the second side of the implant is positioned to contact tissue of the anterior chamber such as the cornea or iris and the first side of the implant is positioned away from the tissue in contact with the aqueous humor.

The transducer assembly 240 may comprise the pressure sensor 212 of distal portion 12 and a telemetric device comprising coil 214 of proximal portion 14. The transducer assembly 240 may comprise the capacitive pressure sensor and inductor on the substrate as described above. The assembly 240 may comprise an elongate flexible substrate that extends so as to support both the proximal portion and the distal portion. The pressure sensor 240 can be encased in a compliant enclosure 246 that is responsive to external pressure. The compliant enclosure 246 may comprise a balloon-like sac made of a biocompatible material that surrounds the transducer assembly 240. Alternatively, the compliant enclosure 246 may comprise a gel, gelatin, or film of biocompatible materials.

The compliant enclosure 246 can be filled with a liquid (or a gel) 250, such as silicone, saline, or other suitable material, that is biocompatible. The properties of the liquid 250 allow the liquid to transmit pressure exerted against the compliant enclosure 246 uniformly against the sensing element of the pressure sensor 212, while isolating the electrical components and circuitry of the transducer assembly 240 from corrosive media.

The illustrated pressure sensor 212 may comprise a known configuration and can be made using known micromachining processes, micro fabrication processes, or other suitable MEMS fabrication techniques. Pressure sensors of this type are commercially available from Motorola, Inc. of Schaumburg, Ill. and TRW Novasensor of Fremont, Calif. It should be understood that many pressure sensors meet the biocompatibility and size requirements and may be used.

The illustrated pressure sensor 212 may comprise a piezoresistive device, and many types of pressure sensors, such as a piezoelectric and capacitive sensors, can be substituted. The pressure sensor 212 may comprises a substrate 260, a sensing diaphragm 262, a plurality of patterned resistors, and a plurality of bond pads, two of which can be associated with each of the resistors.

The substrate 260 may have upper and lower surfaces and can be made of silicon, but could alternatively be made of another suitable material. The substrate 260 has a well region 269 that extends between the upper and lower surfaces and that can be formed using a conventional micro fabrication and bulk micromachining processes including lithography and etching. The sensing diaphragm 262, which extends across the well region 269, can also made of silicon and is defined by the lithography and etching processes. The resistors and the bond pads can be formed from a metal or polysilicon layer that is deposited, patterned, and etched in a known manner on the lower surface 268 of the substrate 260. The resistors could also be formed by doping the silicon using boron, phosphorus, arsenic, or another suitable material to render a region of the silicon with an appropriate conductivity and polarity to create junction-isolated piezoresistors. As will be apparent to those skilled in the art, other methods, such as SIMOX, wafer bonding, and dissolved wafer approaches, could also be used. The resistors can be positioned along the edges of the sensing diaphragm 262 to detect strain in the sensing diaphragm caused by pressure differentials. The resistors could alternatively be positioned in another region of high or maximum strain in the sensing diaphragm 262.

The packaging may be shaped and sized for easy insertion and fixation. For example, the packaging may comprise a first side having a first outer surface and a second side having a second outer surface opposite the first side, in which the first side and the second side extend substantially along a plane, such that the device can be implanted between layers of the sclera. The outer portion comprising the perimeter can be rounded, so as to decrease point localization of forces to the scleral tissue and so as to couple smoothly to the tissue.

Antenna/Reader.

Figure 4A:
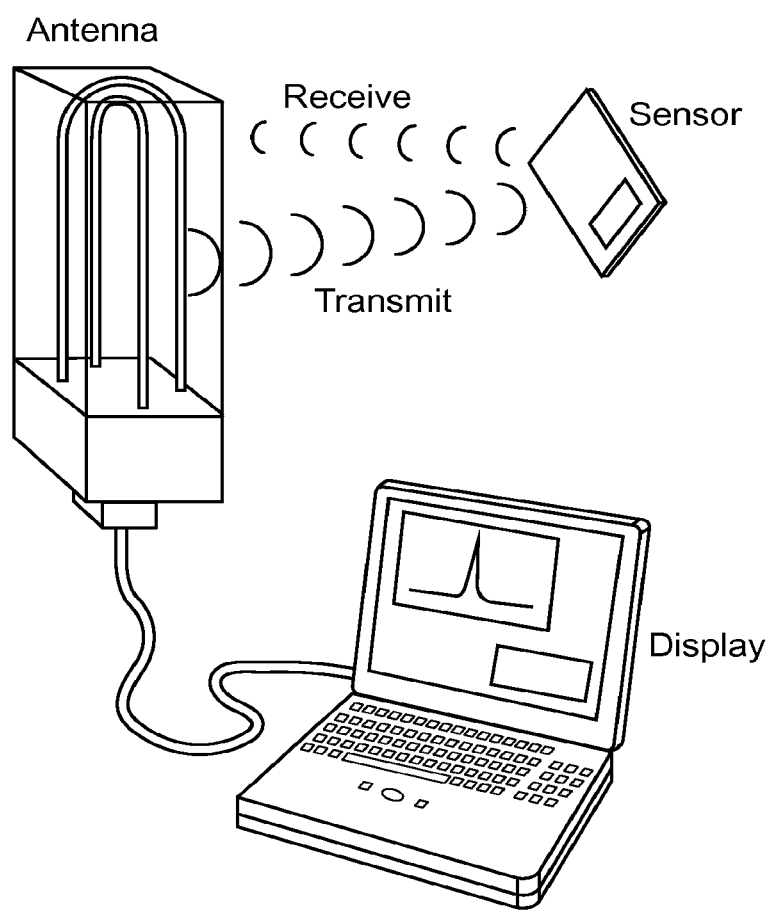
FIG. 4A shows components of an antenna reader, in accordance with embodiments of the present invention.

FIG. 4A shows components of an external reader 310 comprising an antenna/reader and processor coupled to the antenna/reader to determine the IOP. The radio-frequency probe comprises circuitry to emit a radio frequency signal with the antenna so as interrogate the tank circuit of the implanted sensor device, such that the resonant frequency of the LC tank circuit can be determined. As the resonant frequency changes with pressure, the IOP measured with the sensor can be determined based on the resonant frequency. The reader can house the electronics and software, and may comprise a processor having a computer readable medium having instructions of a computer program embodied thereon so as to be used as a data collection, reporting and analysis platform, for example data mining to determine the presence of pressure spikes and trends. The processor can be programmed to measure the IOP and predetermined intervals or predetermined times, or both. The processor can be coupled to the Internet and the servers as described above.

FIG. 4B shows a hand held external reader 310 comprising an antenna reader with components similar to the antenna reader as in 4A. The hand held data reader may comprise the antenna, circuitry to determine the resonant frequency, and circuitry similar to a smart phone such as an iPhone™, such that the hand held reader can measure, store and transmit patient data.

FIG. 4C shows a docking station 319 to receive the hand held antenna reader as in 4B. The docking station can be configured to charge the external reader 310 and may be used to transfer data from the external reader to the remote server. For example, the docking station 319 may comprise serial communication such as a universal serial bus (USB) communication to download measurement data from the external reader 310. The docking station 319 may comprise communication circuitry to transmit the data from the docking station to the remote server, for example one or more of wireless circuitry or wired circuitry.

FIG. 5 shows a method 500 of monitoring a patient. A step 505 measures patient IOP. A step 510 determines that the patient has glaucoma based on IOP and diagnostic tests, for example diagnosis by a physician. A step 515 incises the conjunctiva. A step 520 forms a conjunctival flap to expose sclera. A step 525 forms a channel extending from the conjunctiva through the limbus to the anterior chamber. A step 530 provides the implant, for example to the patient or to the physician. A step 535 positions the implant with the proximal portion on the sclera and the distal portion in the anterior chamber. A step 540 sutures the implant to the sclera. A step 545 covers the implant with flap of conjunctiva and sutures the conjunctiva.

A step 550 measures post-op IOP. A step 551 determines the geographic location of patient. A step 552 determine atmospheric pressure at patient location based on weather and elevation at geographic location. A step 553 adjusts IOP to report based on measured IOP and atmospheric pressure A step 555 measures IOP regularly, for example at least hourly or continuously, to determine the presence of pressure spikes. A step 560 adjusts treatment based on the measured IOP. For example, a physician can adjust dosage of a therapeutic drug or remind the patient to take the medication as prescribed. A step 565 triggers an alarm in response to the measured IOP above predetermined value. A step 580 transmits the data from the patient measurement system to a server located remote from the patient.

At a step 581 a physician prescribes a customized target IOP for the patient with the physician device based on the physician's assessment of the patient. At a step 582, the prescribed customized target IOP is transmitted to from the physician device to one or more of the server or the patient device for comparison with the measured IOP. At a step 583, the physician prescribed customized target IOP is a compared to the measured patient IOP. At a step 584, the physician is notified when the measured patient IOP exceeds the prescribed target IOP, for example with an email from the server to the physician device.

At a step 585, the physician instructs patient based on the measured IOP. For example, the physician may select instructions from a menu. At a step 585A, the physician instructs patient to come into office for visit. At a step 585B, the physician adjusts patient medication. At a step 585C, the physician adjusts target IOP. The physician can identify each of these instructions and select one or more these steps from a menu so as to instruct the patient.

A step 589 analyzes the data at the server, for example with data modeling to determine statistical trends. As the communication from the patient to the physician and back may comprise two way communication routed through the central server, the data available can be useful. The data analysis may comprise mining the patient data with instructions of a computer program embedded on a tangible medium of the remote server. A step 590 shares data among physicians, for example with a registry of patient data for analysis, and physicians of the online physician community can share data with each other.

At a step 591, patients share information and data online, for example with the online community. For example, a family member or care giver can follow up on the care of an elderly patient who shares data with the family member or care giver. At a step 592, a member of the online community can ask questions of physicians, for example the treating physician of the online physician community.

A step 595 transmits a report on the status of the patient to the treating physician, for example to a computer system at the physician's office and/or to a hand held communication device such as an iPhone™ or Blackberry™ or a pager. The report can be transmitted based on the directly measured patient IOP. For example, at a step 595A the report can be generated monthly when the directly measured patient IOP remains within normal limits and at or below the physician prescribed IOP. However, at a step 595B, the treatment report can be generated daily, every few days, or weekly, when the directly measured IOP equals or exceeds the physician prescribed target or when the directly measured IOP exceeds the range of the pre-determined upper and lower limits.

At a step 597, the physician issues a treatment command on the hand held communication device, for example an adjustment to the patient medication.

At a step 599, the above steps are repeated.

It should be appreciated that the specific steps illustrated in FIG. 5 provide a particular method of monitoring a patient, according to an embodiment of the present invention. Other sequences of steps may also be performed according to alternative embodiments. For example, alternative embodiments of the present invention may perform the steps outlined above in a different order. Moreover, the individual steps illustrated in FIG. 5 may include multiple sub-steps that may be performed in various sequences as appropriate to the individual step. Furthermore, additional steps may be added or removed depending on the particular applications. One of ordinary skill in the art would recognize many variations, modifications, and alternatives.

The processor system as described above can be configured to implement many of the steps of method 500. For example, the processor system may comprise a computer readable medium having instructions of a computer program embodied thereon to implement many of the steps of method 500.

Experimental

A person of ordinary skill in the art can conduct experimental studies to determine empirically parameters of the implantable device, such that the device can be implanted for the extended time of at least one year, for example the diameter, the thickness, the curvature and flexibility of each of the proximal portion, the distal portion, and the elongate support extending therebetween. For example, the proximal portion can be implanted above Tenon's capsule of the sclera and below the conjunctiva for an extended period of at least one year. Similar studies can be conducted with additional locations of the eye, for example below Tenon's capsule and above a majority of the thickness of sclera. Such studies can be conducted with an animal model, for example rabbits, and clinical studies with patients may also be conducted.

Experimental Testing with Rabbits

The below described rabbit testing shows successful real time direct measurement of IOP in the rabbit animal model. Similar direct measurements of IOP can be made with the implants as described herein, for example with the coil disposed under the conjunctiva and the pressure sensor disposed in the anterior chamber. The demonstrated direct measurement of intraocular pressure of the aqueous humor and transmission of the electromagnetic pressure signal through the corneal tissue to the external reader correspond substantially to the direct measurement of IOP in the anterior chamber and transmission through the conjunctiva as described herein. For example, the transmission of the measured EM signal through the cornea and aqueous humor disposed between the implanted sensor and external reader comprises a transmission distance through tissue that is at least as much as the tissue transmission distance through the flap of the conjunctiva for the measurement of IOP along the tissue drainage pathway as described herein. Three (3) chip sensors as described herein comprising 6×6 mm Sylgard® encapsulated biosensors were selected for this experiment.

TABLE I

Specifications for Implantable Sensor.

| | |
|---|---|
| Range | 0-50 mm Hg (alternatively 0-60 mm Hg) |
| Mean | 18-25 mm Hg |
| Resolution | 1 mm Hg |
| Working distance | 2-4 cm (alternatively 0-6 cm) |
| Sensor Chip Size | 6 × 6 mm |
| Shape | Square chip, with circular external packaging |
| Accuracy (absolute pressure) | +/−2 mm Hg |

Table I shows exemplary specifications for the implanted device in accordance with embodiments as described herein. The range can be from about 0-50 mm Hg for testing, although other ranges can be used such as 0-60 mm Hg. The mean sensor reading can be within a range from about 18-25 mm Hg. The resolution of the sensor reading can be about 1 mm Hg. The working distance from the measurement probe to the eye can be from about 2-4 cm, although other ranges can be used such as 0-6 mm such that the probe can touch the eyelid. The sensor chip size can be about 6×6 mm square. The shape of the implantable sensor may comprise a square chip with circular external packaging. The absolute accuracy of the sensor device can be +/−2 mm Hg. New Zealand White rabbits (NZW): Surgical procedure:

Three (3) 4-5 kg New Zealand White (NZW) rabbits (2 females, 1 male) were sedated with IM Ketamine HCL (40 mg) and Xylazine HCL (2 mg). A retrobulbar 2% (10 mg) (0.5 ml) was administered to the left eye of 2 animals and to the right eye of the third rabbit. The lids were expose w speculum and topical 0.5% proparacaine HCL and 5% Betadine drops were instilled twice before surgery. A limbal-based conjunctival flap was fashioned superiorly and a limbal groove incision was made with a #15 Bard Parker scalpel. The anterior chamber was entered at 12 o/c with a knife-needle and the wound was enlarged with Castroviejo corneal scissors 3-9 o/c superiorly. The corneal flap was reflected forward with Colibri forceps to exposed the anterior chamber. The implantable sensor was then inserted into the anterior chamber and positioned in-place centrally with McPherson forceps and iris spatula. The wound was then closed with interrupted vertical mattress 6-0 chromic sutures and the conjunctival flap was closed with running 6-0 chromic suture. At the end of the procedure the anterior chambers were observed to have reformed without evidence of any wound leak. Tobrex® (tobramycin 0.3%) was instilled in the superior and inferior cul-de-sac. Rabbits were examined daily by gross and slit-lamp. Topical Tobrex ointment was administered after each examination. The implanted eyes of each animal were judged to be clinically free of post-surgical inflammation by day 5.

In-Vivo IOP Sensing with the Implanted Chip Sensor:

The left eye of one implanted NZW (#15) was selected for in vivo IOP sensing approximately 6 days post-implantation.

Instrumentation Overview:

An implantable chip sensor as described above was implanted in the anterior chamber of the eye of a rabbit, approximately days before measurements were made. The sensors are designed to shift their resonant frequency in response to absolute pressure. The resonant frequency of the implanted sensor is measured by an external reader, which utilizes a custom antenna, a network analyzer, and a custom software application running on a PC. Prior to implantation, the pressure-frequency response of the sensor is characterized, and is saved in a calibration file on the PC. After implantation, the software uses the network analyzer to measure the center frequency of the sensor, then uses the calibration file to convert frequency to pressure.

Figure 6A:
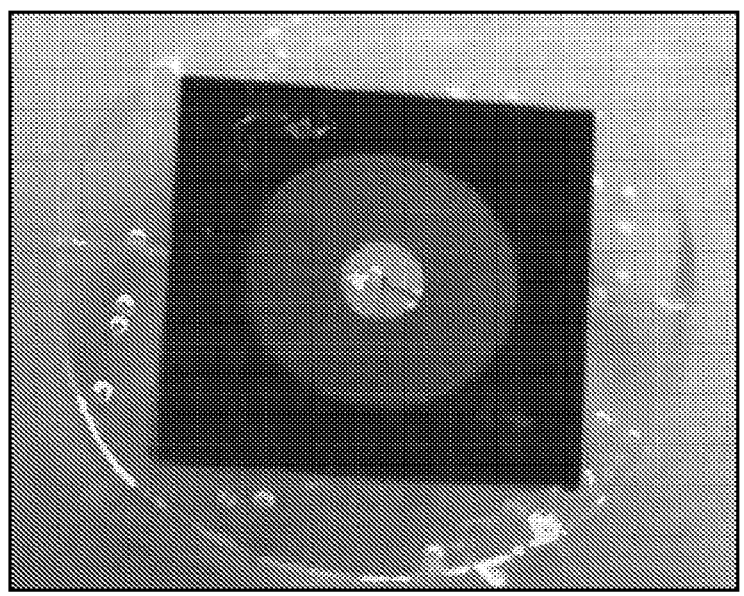
FIG. 6A shows an implantable sensor package for direct measurement of IOP prior to placement in an eye of a rabbit, in accordance with embodiments of the present invention.

Instrumentation Setup:
  Setup Materials & Equipment:
Orthogonal antenna
Vector Network Analyzer (VNA, HP 8753C)
  VNA—antenna interface hardware
Directional coupler, 1 OdB, (Olektron A2655-03)
  4 db N type attenuator
  Antenna tuner & balun (custom)
Splitter (Minicircuits ZFSCJ-2-1-S)
Receiver amplifier (+34 dB, Qbit QB-164-LH)
Lowpass filter (Minicircuits BLP-100+
Coaxial cables with SMA terminations
Clamp-on ferrites (3ea, Fair-rite 0443665806)
  Antenna compensation coil (custom)
  Lab stand (for holding antenna)
Laptop PC (Dell D610)
  Data acquisition and frequency-pressure conversion software (Custom, AcuMEMs)
GPIB-USB adapter (National Instruments)
  Tonometer (for external IOP measurement): iCare tonometer TA01 i
Setup Procedure:
  Place the antenna on a non-metallic table (the surface may not contain a conductive loop—e.g. a metal frame around the perimeter of the table).
  "Null" the antenna
    Adjust the orthogonal antenna position to minimize cross coupling (minimize background signal on the VNA)
  Adjust the tuner to achieve nominal "flatness" in the 40-50 MHz region
  Compensate the effect of the patient body
    Place the patient, with the un-implanted eye near the antenna
    Adjust the compensation coil position to again minimize the background
    Start the pressure-logging software on the PC, and load the sensor file.
Procedure:
The patient was anaesthetized to minimize rapid movements during data acquisition The implanted eye was moved close (within 5 mm) to the antenna.
The software recorded data during the following protocol
  Confirm detection of the sensor in V A manual mode
  Run acquisition for several minutes to establish a baseline
  Use soft-tipped swab to externally apply pressure to the sclera of implanted eye Minimize any repositioning of the patient's head when applying pressure
  Maintain applied pressure, with as much stability as possible, for a few minutes
  Gently remove the swab
  Continue to record data for several more minutes
  Repeat the above pressure application (discretionary)
Data:
Sensor characterization before implantation:
Date of characterization: XX/XX/XXXX
Nominal center frequency (at local atmospheric pressure):
Conditions:
encapsulated in silicone elastomer comprising Sylgard™ 529
  placed inside of a small PVC pressure chamber
  container placed directly on side of antenna cover
sensor approx. 5 mm from antenna cover Pressure-Frequency Characterization:
Measured scale factor: −0.06612 MHz/psi
x 0.019337 psi/mmHg=−0.0012786 MHz/Hg
 Null frequency (0 PSI gauge): 45.12 MHz Sensor in-vivo measurements:
Sensor characterization after implantation:
Date, Time: XX/XX/XXXX
Local pressure: 29.78 in. Hg
Animal description: Rabbit, female, approx. 4 kg, approx. 12 wks old
Implantation site: anterior chamber of left eye, sensor #XXX-Y-ZZ FIG. 6A shows an implantable sensor for direct measurement of IOP prior to placement in an eye of a rabbit. The implantable sensor device comprises a chip sensor comprising a capacitive sensor and coil embedded in a complaint transparent enclosure as described above. The substrate supporting the coil comprises an approximately 6 mm by 6 mm square having the circular coil and capacitor disposed thereon. The substrate and circuitry comprise a thickness of about 250 um and the total thickness with the complain enclosure comprises about 500 um. The circular complaint enclosure comprise a circular perimeter and a diameter of about 7 mm, such that the complaint enclosure extends around and covers the corners of the substrate with a clearance of about 0.5 mm on each corner.

Figure 6B:
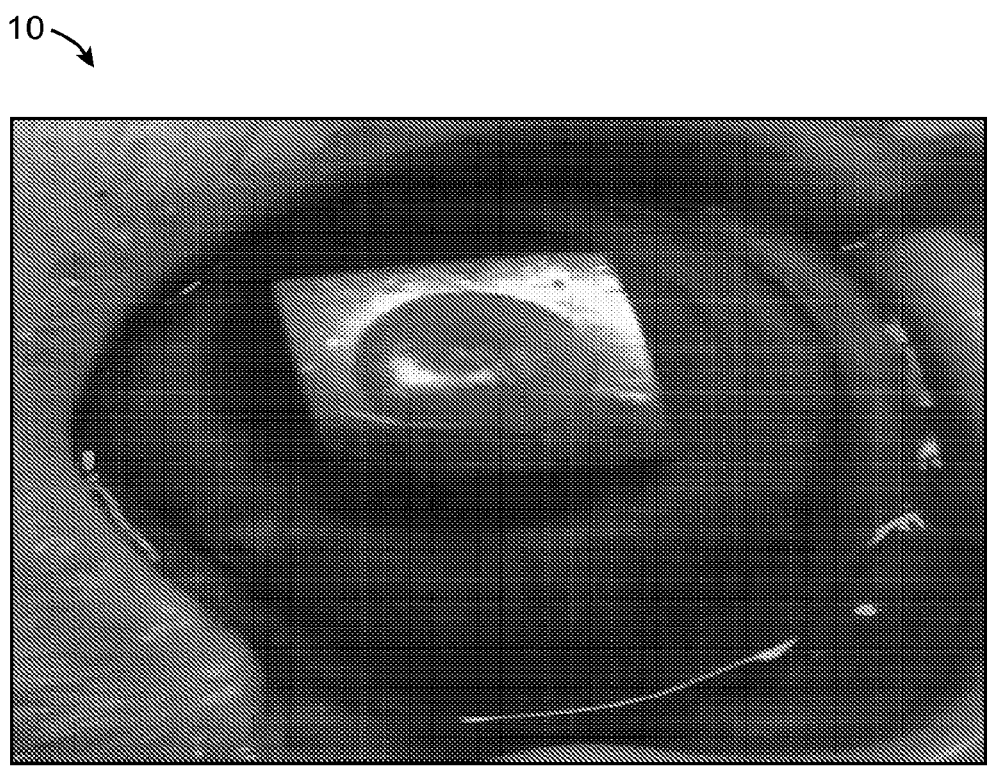
FIG. 6B shows the experimentally tested implantable sensor as in FIG. 6A implanted in the anterior chamber of an eye of a rabbit.

FIG. 6B shows the experimentally tested implantable sensor as in FIG. 6A implanted in the anterior chamber of an eye of a rabbit. The sensor is implanted under the cornea and above the pupil and can be readily seen in the eye of the rabbit.

Figure 6C:
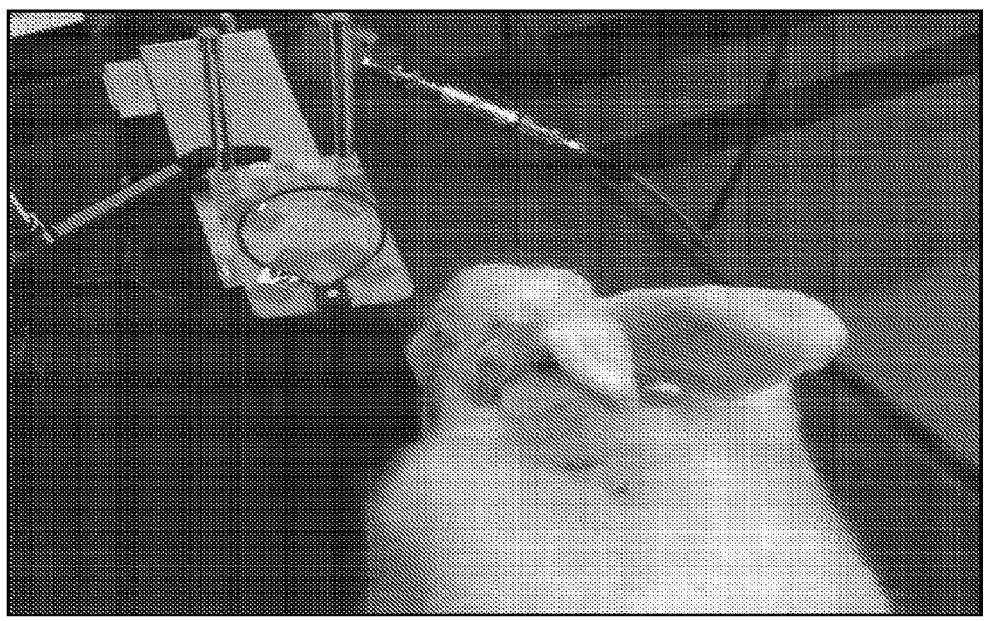
FIG. 6C shows a rabbit positioned near an antenna reader with the sensor implanted as in FIGS. 6A and 6B.

FIG. 6C shows a rabbit positioned near an antenna reader with the sensor implanted as in FIGS. 6 A and 6B. The head of the rabbit is positioned near the telemetry coil of the reader for direct measurement of IOP.

Figure 6D:
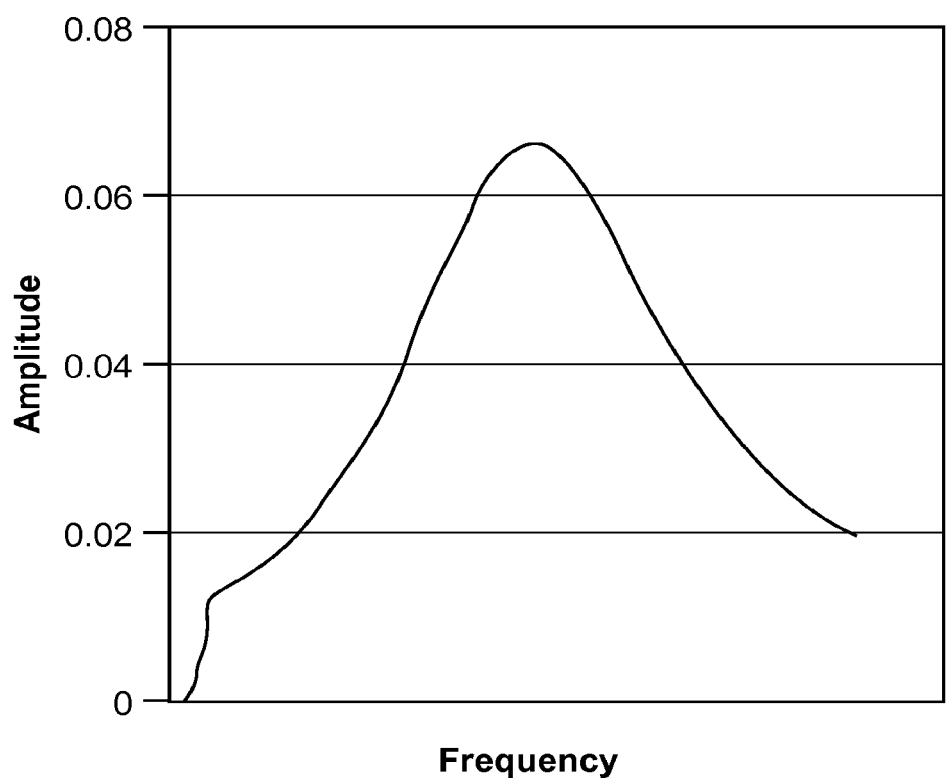
FIG. 6D shows a distribution of sensor signals and a peak of the distribution for IOP measured directly with the rabbit positioned near the sensor as in FIG. 6C.

FIG. 6D shows a distribution of sensor signals and a peak of the distribution for IOP measured directly with the rabbit positioned near the sensor as in FIG. 6C. The peak of the distribution corresponds to a measured IOP of about 3 mm of Hg. This direct measurement of IOP compared well with a known veterinary tonometer (Icare™ VET) commercially available from Icare of Finland.

Figure 6E:
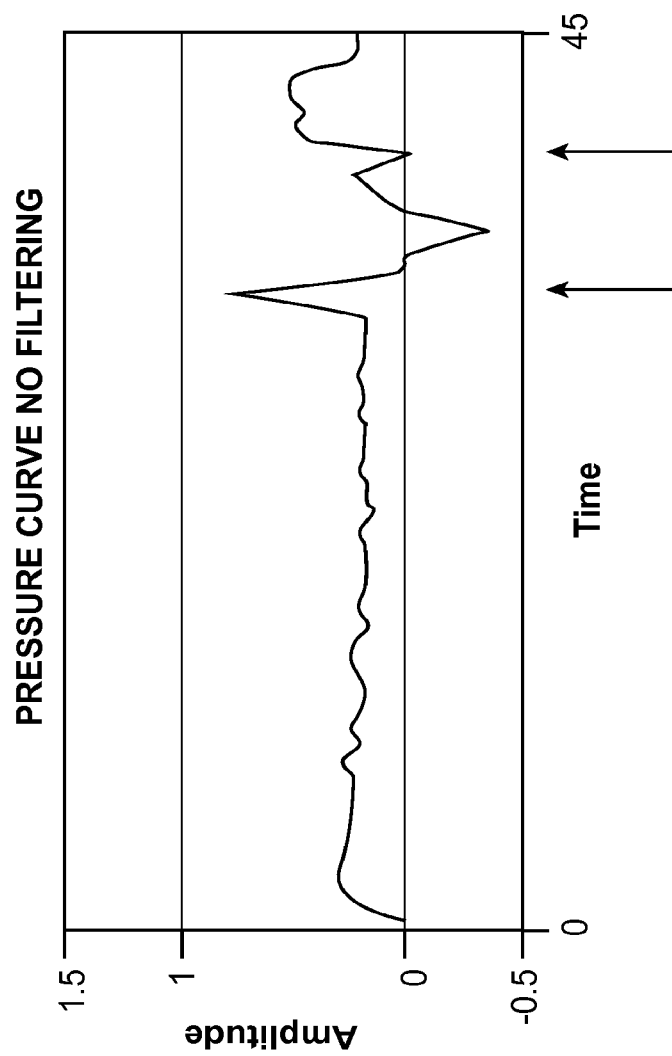
FIG. 6E shows pressure shifts of IOP measured directly over time with the rabbit positioned near the sensor reader as in FIG. 6C.

FIG. 6E shows pressure shifts of IOP measured directly over time with the rabbit positioned near the sensor reader as in FIG. 6C. The amplitude signal corresponds to the IOP of the eye and is measured in units that correspond to mm of Hg. The direct IOP measurement is shown for about 45 seconds. The amplitude of the signal (arbitrary units) goes from −0.5 to 1.5, and 0 corresponds to an IOP of 0. The signal from about 5 seconds to about 30 s has an amplitude of about 0.2 to 0.3 and corresponds to an IOP of about 3 to 4 mm of Hg. To evaluate the real time response of the implanted sensor, the eye was touched with a Q-tip™ cotton swap at about 30 seconds (shown with first vertical arrow), and the measured IOP elevated substantially. The Q-tip™ was removed and the measured IOP went negative. The Q-tip™ cotton swap was applied again at about and the pressure similarly elevated (shown with second vertical arrow). The directly measured IOP increase was verified with the external tonometer that showed an IOP of about 13 mm Hg. Upon removal of the cotton swab, the IOP decreased to about 3-4 mm Hg at 45 seconds.

IOP measurements using iCare tonometer:
 Initial IOP of unimplanted eye: 6 mmHg
Initial IOP of implanted eye: 3 mmHg
Pressure Change Test on Implanted Eye:
 3 mmHg (initial pressure)
16 mmHg (with swab applying pressure to sclera)
 21 mmHg (2nd measurement with swab applying pressure to sclera)
Recorded Data from "Reader":
 Fc used for measurements: 45.0 MHz (center of scan range—not necessarily 0 psi frequency)
 Span used for measurement: 5.0 MHz Changes in the center frequency of the sensor are produced by changes in absolute pressure. To resolve relative (gauge) pressure, local atmospheric pressure can be accounted for. The data in the graph was manually adjusted for offsets in MS Excel. Time is not scaled in the graph, but each point represents approximately 15 seconds between acquisitions. Changes in center frequency can also result from other environmental effects, including presence of nearby metal, the patient body, and motion artifacts. It can be important to minimize motion artifacts, to avoid placing the antenna near metal objects, and to compensate for the effects of the patient body (using the compensation coil). The large excursions around samples 22-30 in FIG. 6F are motion artifacts, for example.

The signal from the sensor was readily detectable at approximately 45 MHz. During the testing, the frequency shifted readily (downward) with the application of pressure on the sclera (using a swab). The corresponding pressure shifts, as measured by the sensor and reader, were larger than similar readings taken subsequently with the tonometer.

Figure 6F:
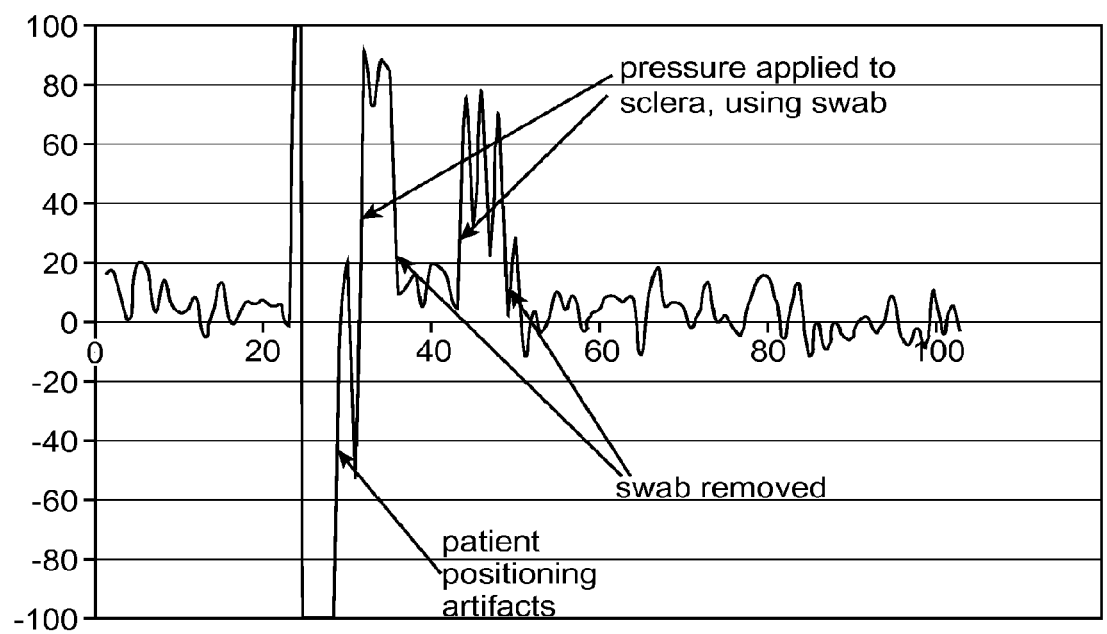
FIG. 6F shows IOP measured directly over time with calibration for the rabbit positioned near the sensor reader as in FIG. 6C.

FIG. 6F shows IOP measured directly over time with calibration for the rabbit positioned near the sensor reader as in FIG. 6C. Direct measurement of IOP is shown to about 100 seconds, and the calibrated measured IOP is shown in mm of Hg. The measurements show increases in measured IOP when the swap if applied to the sclera, and decreases in the directly measured IOP when the swab is removed. Although some measurement artifacts are shown, the data can be filtered to remove these artifacts, for example with digital filtering. Also, lower IOP after applied pressure is consistent with recovery of the eye and ocular tissues.

CONCLUSIONS

The implantable, wireless sensors are capable of measuring intra-ocular pressure changes. Further testing can characterize the absolute and relative accuracies of the sensor and reader measurements over the range, for example simultaneous external indirect measurements and internal direct measurements.

Although the above experiments show good signal measurements, one of ordinary skill in the art can make improvements. For example, it may be helpful to strengthen the signal from the sensor and enhance its sensitivity to pressure. Also, the sensor and reader may be configured so as to have less sensitive to environmental effects.

While the exemplary embodiments have been described in some detail, by way of example and for clarity of understanding, those of skill in the art will recognize that a variety of modifications, adaptations, and changes may be employed. Hence, the scope of the present invention shall be limited solely by the appended claims and the full scope of the equivalents thereof.

What is claimed is:

1. An implantable device for measuring an intraocular pressure of an eye having an anterior chamber and a conjunctiva, the implantable device comprising:
 a distal portion comprising a pressure sensor,
 a proximal portion comprising a coil; and
 a conformable elongate support extending between the distal portion and the coil to couple the distal portion to the coil and wherein the conformable elongate support is sized to position the sensor in the anterior chamber when the proximal portion is positioned under a conjunctiva of the eye, wherein the pressure sensor comprises a pressure transducer for placement in the anterior chamber and responsive to pressure of the anterior chamber and comprises a compliant enclosure encapsulating the pressure sensor, wherein the compliant enclosure is filled with a conformable material comprising one or more of a liquid, viscous material, or gel and the compliant enclosure is configured to be positioned in the anterior chamber such that the conformable material transmits pressure exerted on the compliant enclosure to the pressure transducer, and wherein the conformable material is positioned over the pressure transducer such that pressure exerted on the compliant enclosure in any direction is exerted uniformly on one or more of a first side or a second side of the pressure sensor.

2. The implantable device of claim 1, wherein the pressure sensor comprises a capacitor responsive to the intraocular pressure, the capacitor having a first side and a second side, and wherein the conformable material is disposed over the first side and the second side such that the capacitive sensor is responsive to pressure on each of the first side and the second side when positioned in the anterior chamber.

3. The implantable device of claim 2, wherein the capacitor is encapsulated with the conformable material.

4. The implantable device of claim 2, wherein the distal portion comprises a maximum cross-sectional size of no more than about 0.5 mm.

5. The implantable device of claim 1, wherein the proximal portion comprises a coil coupled to the pressure sensor such that the coil is positioned under the conjunctiva when the distal portion is positioned in the aqueous humor.

6. The implantable device of claim 5, wherein the coil comprises a substantially single loop antenna coil coupled to a second coil having a plurality of turns.

7. The implantable device of claim 5, wherein the coil is disposed on a substrate and wherein the substrate comprises a curved shape so as to conform to a curvature of the eye.

8. The implantable device of claim 7, wherein the proximal portion comprises a lower concave surface to contact a sclera of the eye and an upper convex surface to contact the conjunctiva of the eye such that the upper convex surface and the lower concave surface correspond to the curvature of the eye when the distal portion is inserted into the anterior chamber.

9. The implantable device of claim 8, wherein the upper convex surface has a curvature corresponding substantially to the curvature of the eye and wherein the lower concave surface has the curvature corresponding substantially to the curvature of eye, such that the proximal portion is retained between the sclera and the conjunctiva with the conjunctiva extending over the upper surface when the distal portion is positioned in the anterior chamber.

10. The implantable device of claim 5, wherein the coil is joined to the pressure sensor with the conformable material further extending between the coil and the pressure sensor.

11. The implantable device of claim 5, wherein the coil is attached to the pressure sensor with the conformable material extending between the coil and the pressure sensor.

12. The implantable device of claim 5, wherein the proximal portion comprises a maximum distance across of no more than about 15 mm.

13. The implantable device of claim 5, wherein the proximal portion comprises a maximum distance across of no more than about 10 mm.

14. The implantable device of claim 5, wherein the proximal portion comprises a maximum distance across of no more than about 6 mm.

15. The implantable device of claim 5, wherein the proximal portion comprises a maximum thickness across of no more than about 1 mm.

16. The implantable device of claim 5, wherein the proximal portion comprises a maximum thickness of no more than about 0.5 mm.

17. The implantable device of claim 1, wherein the distal portion comprises a maximum thickness of no more than about 0.5 mm.

18. The implantable device of claim 1, wherein the conformable elongate support comprises an intermediate portion having a length of no more than about 10 mm.

19. The implantable device of claim 1, wherein the conformable elongate support comprises an intermediate portion having a cross sectional size within a range from about 1 to 3 French.

20. The implantable device of claim 1, wherein the conformable elongate support comprises an intermediate portion having a conformable tube extending between the proximal portion and the distal portion and wherein the tube is disposed over a conformable conductor and substrate extending from the pressure sensor to the proximal portion.

21. The implantable device of claim 1, wherein the pressure sensor and the coil are disposed on a substrate such that the coil is coupled to the sensor with the substrate and wherein the conformable elongate support comprises an intermediate portion of the substrate disposed between the proximal portion and the distal portion and wherein the intermediate portion of the substrate is composed of a material having a thickness and a width such that the intermediate portion is capable of conforming to the eye.

* * * * *